United States Patent
Meardi et al.

(10) Patent No.: US 12,219,160 B2
(45) Date of Patent: Feb. 4, 2025

(54) DECODER DEVICES, METHODS AND COMPUTER PROGRAMS

(71) Applicant: V-NOVA INTERNATIONAL LIMITED, London (GB)

(72) Inventors: Guido Meardi, London (GB); Simone Ferrara, London (GB); Gaurav Mittal, London (GB)

(73) Assignee: V-NOVA INTERNATIONAL LIMITED, London (GB)

( * ) Notice: Subject to any disclaimer, the term of this patent is extended or adjusted under 35 U.S.C. 154(b) by 0 days.

(21) Appl. No.: 18/161,721

(22) Filed: Jan. 30, 2023

(65) Prior Publication Data

US 2023/0336755 A1 Oct. 19, 2023

Related U.S. Application Data

(63) Continuation of application No. 17/173,941, filed on Feb. 11, 2021, now Pat. No. 11,570,454, which is a
(Continued)

(30) Foreign Application Priority Data

Jul. 20, 2016 (GB) .................................. 1612585
Feb. 12, 2020 (GB) .................................. 2001926

(51) Int. Cl.
*H04N 19/30* (2014.01)
*A61B 90/00* (2016.01)
(Continued)

(52) U.S. Cl.
CPC ........... *H04N 19/30* (2014.11); *A61B 90/361* (2016.02); *G16H 30/20* (2018.01); *G16H 40/67* (2018.01);
(Continued)

(58) Field of Classification Search
USPC ...................................................... 375/240.01
See application file for complete search history.

(56) References Cited

U.S. PATENT DOCUMENTS

| | | | |
|---|---|---|---|
| 6,252,989 B1 | 6/2001 | Geisler et al. | |
| 2003/0072375 A1* | 4/2003 | Soundararajan | H04N 19/30 375/E7.092 |

(Continued)

FOREIGN PATENT DOCUMENTS

| | | | |
|---|---|---|---|
| WO | 2012-015460 | 2/2012 | |
| WO | 2013-011492 | 1/2013 | |
| WO | WO-2013011492 A2 * | 1/2013 | ........... H04N 19/105 |

OTHER PUBLICATIONS

Boyce, et al., "Overview of SHVC: Scalable Extensions of the High Efficiency Video Coding Standard", Jan. 1, 2016.
(Continued)

*Primary Examiner* — Behrooz M Senfi
(74) *Attorney, Agent, or Firm* — Workman Nydegger

(57) ABSTRACT

A medical telepresence system comprising: an interface to receive a plurality of data feeds from a live medical procedure, at least one data feed comprising a video signal capturing the live medical procedure; a hierarchical encoder to encode the plurality of data feeds using a first tier-based hierarchical data coding scheme, wherein encoded data from the hierarchical encoder is decodable by a first set of computing devices for viewing, the first set of computing devices being communicatively coupled to the hierarchical encoder using a first network connection; a transcoder to convert from the first tier-based hierarchical data coding scheme to a second tier-based hierarchical data coding scheme, wherein encoded data from the transcoder is receivable by a second set of computing devices for viewing, the second set of computing devices being communicatively coupled to the transcoder using a second network connec-
(Continued)

tion, the second network connection being of a lower quality than the first network connection; and a recorder to store the output of the hierarchical encoder as a set of tier-based files for later retrieval, wherein each of the set of tier-based files represent different levels of quality.

18 Claims, 17 Drawing Sheets

Related U.S. Application Data continuation-in-part of application No. 16/252,362, filed on Jan. 18, 2019, now Pat. No. 11,277,625, which is a continuation of application No. PCT/GB2017/052142, filed on Jul. 20, 2017.

(51) Int. Cl.
  *G16H 30/20*    (2018.01)
  *G16H 40/67*    (2018.01)
  *H04N 5/76*     (2006.01)
  *H04N 7/025*    (2006.01)
  *H04N 7/08*     (2006.01)
  *H04N 19/167*   (2014.01)
  *H04N 19/40*    (2014.01)

(52) U.S. Cl.
  CPC ............... *H04N 5/76* (2013.01); *H04N 7/025* (2013.01); *H04N 7/0806* (2013.01); *H04N 19/167* (2014.11); *H04N 19/40* (2014.11)

(56) References Cited

U.S. PATENT DOCUMENTS

| | | |
|---|---|---|
| 2006/0189886 A1 | 8/2006 | Jones et al. |
| 2011/0002383 A1* | 1/2011 | Yoshida ............... H04N 19/70 375/E7.243 |
| 2011/0096990 A1* | 4/2011 | Lu ....................... H04N 19/136 382/233 |
| 2012/0154557 A1 | 6/2012 | Perez et al. |
| 2013/0101015 A1 | 4/2013 | He et al. |
| 2013/0195169 A1 | 8/2013 | Jang et al. |
| 2013/0322530 A1 | 12/2013 | Rossato et al. |
| 2014/0247277 A1 | 9/2014 | Guenter et al. |
| 2014/0361977 A1 | 12/2014 | Stafford et al. |
| 2015/0281709 A1 | 10/2015 | Bracha et al. |
| 2015/0373341 A1* | 12/2015 | Davies ............... H04N 19/139 375/240.02 |
| 2016/0234482 A1 | 8/2016 | Bickerstaff et al. |
| 2017/0026653 A1 | 1/2017 | Xie et al. |
| 2017/0118466 A1 | 4/2017 | Nakagami |
| 2017/0359586 A1 | 12/2017 | Xue et al. |
| 2019/0215133 A1 | 7/2019 | Pan et al. |
| 2021/0076966 A1 | 3/2021 | Grantcharov et al. |

OTHER PUBLICATIONS

Einarsson et al., "Mixed Resolution Video Coding for Low Bit-Rate Channels", Jul. 28, 1997.
UKIPO Search Report dated Jan. 23, 2017 for Application No. GB 1612585.8.
International Search Report and Written Opinion for PCT/GB2017/052142 mailed Nov. 17, 2017.
EP Search Report dated Jun. 15, 2021 for Application No. 17 752 418.8.
Final Office Action received for U.S. Appl. No. 16/252,362, mailed on Aug. 11, 2020, 12 pages.
International Preliminary Report on Patentability received for PCT Patent Application No. PCT/GB2017/052142, mailed on Jan. 31, 2019, 9 pages.
Non-Final Office Action received for U.S. Appl. No. 16/252,362, mailed on Jun. 3, 2021, 13 pages.
Notice of Allowance received for U.S. Appl. No. 16/252,362, mailed on Nov. 5, 2021, 9 pages.
Notice of Allowance received for U.S. Appl. No. 17/173,941, mailed on May 11, 2022, 8 pages.
Notice of Allowance received for U.S. Appl. No. 17/173,941, mailed on Oct. 5, 2022, 9 pages.

* cited by examiner

DECODER DEVICES, METHODS AND COMPUTER PROGRAMS

RELATED CASES

The present application is a continuation of U.S. patent application Ser. No. 17/173,941, filed Feb. 11, 2021 which is a continuation-in-part of U.S. patent application Ser. No. 16/252,362, filed Jan. 18, 2019, which issued as U.S. Pat. No. 11,277,625 on Mar. 15, 2022, which claims priority to International Patent Application No. PCT/GB2017/052142, filed Jul. 20, 2017, which claims priority to UK Patent Application No. 1612585.8, filed Jul. 20, 2016. The present application also claims priority to UK Patent Application No. 2001926.1, filed Feb. 12, 2020. The entire disclosures of the aforementioned patent applications are disclosed herein by reference.

TECHNICAL FIELD

The present invention relates to devices, methods and computer programs for allowing telepresence via the use of hierarchical video and image coding.

BACKGROUND

In recent years, the modern world has become increasing global. This has resulted in an increasing number of cases where there is a desire for experts to provide remote guidance. For example, medicine, law, finance, and engineering often require a globally distributed team to work on a common project. This may include the use of expert witnesses in legal proceedings, consultants in surgical procedures, forensic experts in insurance and law enforcement investigations. There is also a need to review materials from team projects, such as conference materials or recordings of experiments, surgery or meetings, for an audit and training perspective. For example, the expertise involved may be a scarce resource, and so recordings from remote guidance sessions may be a valuable resource for training and educational.

Within these applications there are often common requirements. For example, there is often a requirement to render data visually, and to be able to navigate the data. For example, it may be desired to be able to pan and zoom and scroll backwards and forwards within a data set. The data set may be a video source (e.g. a recording from a camera), a virtual video source (e.g. a virtual or augmented reality environment), or an interactive 2D or 3D data visualisation (e.g. where portions of the visualisation may be changeable over time, similar to a video). In certain case, the dataset may consist of hyperspectral still and moving imagery (e.g. visualisations of electromagnetic radiation outside of the visual spectrum) and/or stereoscopic imagery (e.g. pairs of image sequences designed for the left and right eyes). In certain cases, a viewer or consumer of the imagery needs to be able to pan and zoom and stream relevant sections of the imagery, as well as index forwards and backwards on a frame by frame basis. This is often difficult with current data streaming technologies, e.g. it may be difficult to change the stream on-the-fly and/or quickly skip to different portions of the stream or a field of view. Furthermore, there is a limitation of constrained and contested datalinks, which often means that quality has to be sacrifices or delay introduced, which in turn may remove the value from the information and constrain the use cases for telepresence and remote guidance.

Comparative video streaming solutions that are used for remote guidance typically use compression to stream video and images for live transfer and storage. These comparative solutions may use either Intra or Group of Pictures (GoP) compression of the images or frames in their entirety. Comparative solutions are often based on existing video codecs. These technologies encode the entire frame or image as a single monolithic block, which has to be transported, stored, accessed and decoded as an entire image, frame or GoP—even when only a part of the image or cut-out is required.

SUMMARY OF INVENTION

According to a first aspect, there is provided a medical telepresence system as recited in independent claim 1.

According to a second aspect, there is provided a method for medical telepresence as recited in independent claim 8.

According to one aspect, there is provided a non-transitory computer readable medium storing instructions that when executed by a processor cause the processor to perform one of the methods described herein.

Preferred embodiments are recited in the dependent claims. Other non-claimed aspects are also described below.

DETAILED DESCRIPTION

Certain examples described herein use a hierarchical data coding scheme to provide telepresence and/or remote guidance systems. The hierarchical data coding scheme may be one or more of the SMPTE VC-6 standard and the MPEG-5, Part-2, LCEVC standard. Hierarchical data coding schemes such as SMPTE VC-6 standard use a hierarchy of resolutions to encode data, such that each image or frame in a sequence (such as a video or supplied rendering of an interactive visualisation) is represented at a plurality of layers or echelons. In certain cases, the hierarchical data coding scheme may encode a layer of data as residual data, that represents a difference between a first original or desired signal for the layer and a second reconstructed signal for the layer (e.g. a lower layer signal that is upsampled and/or a processed signal that results from one or more of encoding and decoding).

Certain examples described herein may allow region-of-interest decoding and/or pan-or-zoom functionality using different levels or layers of representations in the hierarchical data coding schemes. For example, a lower or lowest level or layer of encoding may be transmitted for a complete field of view, but higher levels or layers of encoding may only be transmitted and/or decoded for particular regions of interest, current viewpoints or current regions of zoom. In these cases, the underlying system may only transfer and decode the spatial resolutions and regions that a user is viewing, rather than the entire frame (e.g. of a video, or view of a visualisation or immersive environment).

Figure 1:
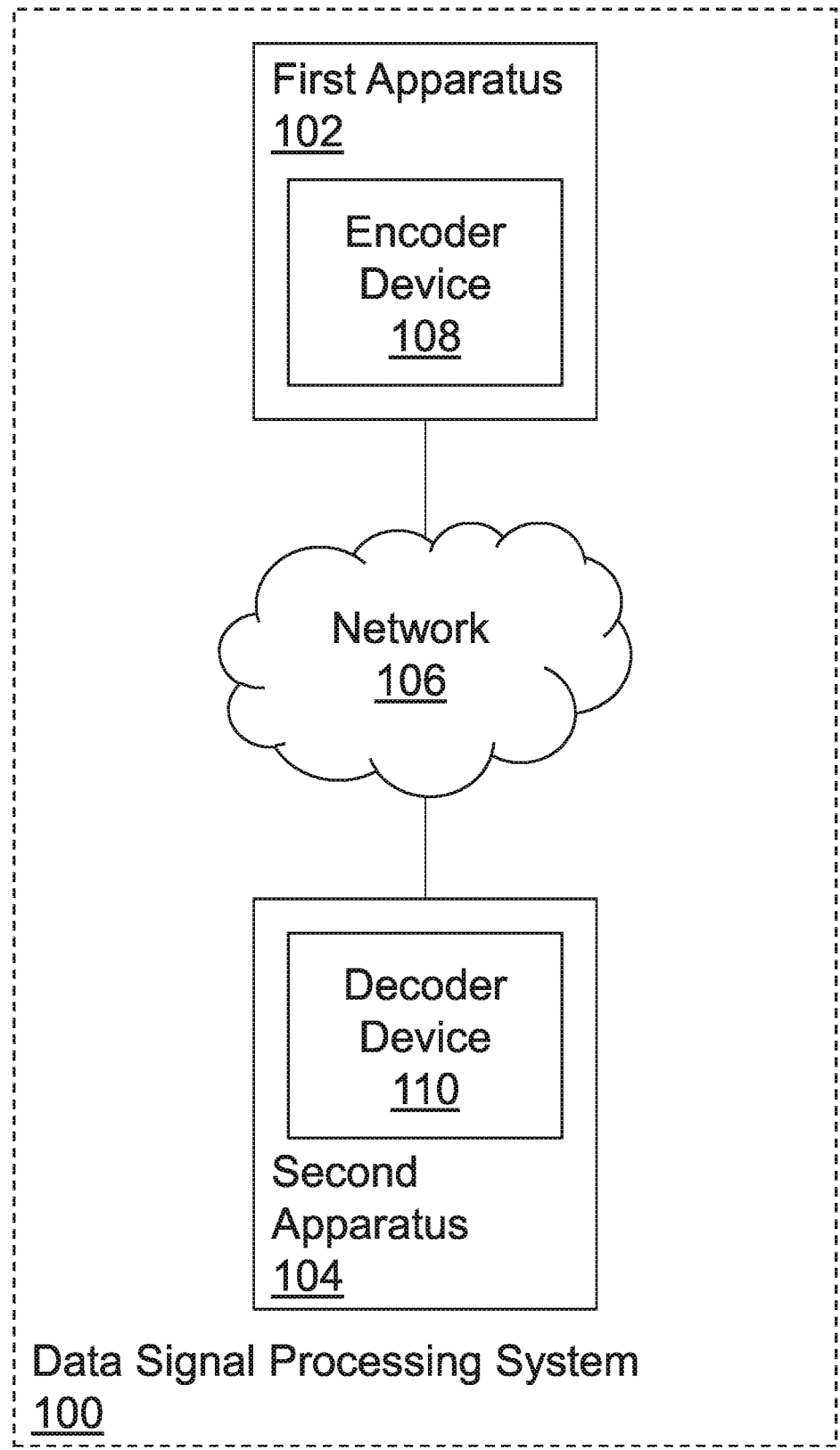
FIG. 1 shows a schematic block diagram of an example of a data signal processing system in accordance with an example.

Referring to FIG. 1, there is shown an example of a data signal processing system 100. The data signal processing system 100 is used to process a data signal. A data signal is a signal that carries and/or represents data. For convenience and brevity, in the specific examples described in more detail below, the data signal is typically image data and/or video data, it being understood that a data signal may be of a different type. For example, a data signal may be an audio signal. An audio signal carries audio data. The data signal may be an ultrasonic signal associated with medical ultrasound equipment. The data signal may comprise a view of a virtual and/or augmented reality environment. The data signal may comprise one or more video feeds from a medical procedure, experiment, or video conference. The data signal may comprise a combination of video and visualisations, e.g. a video feed of an object and a corresponding 3D model of the object. Other examples of data signals include, but are not limited to, multi-view video signals (such as three-dimensional video), volumetric signals such as those used in medical, scientific or holographic imaging, or other multi-dimensional signals.

The data signal processing system 100 includes a first apparatus 102 and a second apparatus 104. The first apparatus 102 and second apparatus 104 may have a client-server relationship, with the first apparatus 102 performing the functions of a server device and the second apparatus 104 performing the functions of a client device. The data processing system 100 may include at least one additional apparatus. The first apparatus 102 and/or second apparatus 104 may comprise one or more components. The components may be implemented in hardware and/or software. The one or more components may be co-located or may be located remotely from each other in a distributed arrangement in the data signal processing system 100.

In some examples, the first apparatus 102 and/or second apparatus 104 comprises or is comprised in virtual reality equipment. Examples of virtual reality equipment include, but are not limited to, virtual reality headsets and virtual reality goggles. Virtual reality is also known as augmented reality or immersive multimedia. Virtual reality is a computer technology that generates, augments or replicates an environment and simulates a user's physical presence in that environment.

In some examples, first apparatus 102 and/or second apparatus 104 comprises or is comprised in medical imaging equipment. Medical imaging is used to generate visual representations of all or part of a body, in order to facilitate clinical analysis and treatment, and can include generating images of specific organs or cells of the body. Examples of medical imaging equipment include, but are not limited to, ultrasound equipment, magnetic resonance imaging (MRI) equipment, X-ray computed tomography (CT) equipment, positron emission tomography (PET) equipment and functional near-infrared spectroscopy (FNIR) equipment.

In some examples, the first apparatus 102 and/or second apparatus 104 comprises or is comprised in machine vision equipment. Machine vision equipment allows a machine to obtain visual information relating to the machine's surroundings. An example of machine vision equipment is a smart camera. Another example of machine vision equipment is a robotic equipment.

In some examples, the first apparatus 102 and/or second apparatus 104 comprises or is comprised in a mobile communications device. A mobile communications device is a device configured to be used for mobile communications, for example using a cellular and/or a wireless network. Examples of mobile communications devices includes, but are not limited to, smartphones and tablet computing devices.

The first and/or second apparatus 102, 104 may be powered by an internal battery. The internal battery may be a rechargeable battery. Battery usage considerations may be relevant in such cases. Alternatively or additionally, the first and/or second apparatus 102, 104 may be powered by an external power source.

The first apparatus 102 is communicatively coupled to the second apparatus 104 via one or more data communications networks 106. Examples of the data communications network 106 include, but are not limited to, the Internet, a Local Area Network (LAN) and a Wide Area Network (WAN). The first and/or second apparatus 102, 104 may have a wired and/or wireless connection to the data communications network 106.

In certain examples, there may be one or more versions of the first apparatus 102 and a plurality of equipment that are implemented as per the second apparatus 104. For example, a video feed for a medical procedure such as surgery may be encoded using a first server device acting as a first apparatus and a second server device acting as a second apparatus may supply a 3D model and/or data related to an object being viewed (e.g. as results from artificial intelligence—AI—analysis that may be provided as an augmented or stand-alone visual layer).

Encoders and Decoders

The first apparatus 102 comprises an encoder device 108. The encoder device 108 is configured to encode a data signal, for example image data and/or video data. The encoder device 108 may perform one or more further functions in addition to encoding a data signal. The encoder device 108 may be embodied in various different ways. For example, the encoder device 108 may be embodied in hardware and/or software.

The second apparatus 104 comprises a decoder device 110. The decoder device 110 is configured to decode a data signal, for example image data and/or video data. The decoder device 110 may perform one or more further functions in addition to decoding a data signal. The decoder device 110 may be embodied in various different ways. For example, the decoder device 110 may be embodied in hardware and/or software.

The encoder device 108 encodes a data signal and transmits the encoded data signal to the decoder device 110 via the data communications network 106. The decoder device 110 decodes the received, encoded data signal and generates a decoded data signal. The decoder device 110 may output the decoded data signal, or data derived using the decoded data signal. For example, the decoder device 110 may output such data for display on one or more display devices associated with the second apparatus 104. The one or more display devices may form part of the second apparatus 104 or may be otherwise associated with the second apparatus 104. Examples of display devices include, but are not limited to, a head-mounted display (HMD), an optical head-mounted display (OHMD), smart glasses, a virtual retinal display (VRD), a mobile phone or tablet display, a computer screen, a video monitor, an oscilloscope screen, etc.

The encoder device 108 may be arranged to encode a data signal and transmit this to multiple decoder devices, wherein each decoder device may receive a common stream or a different stream. In one case, different decoder devices may decode different portions of a common stream, e.g. different levels or layers of quality so as to reconstruct an original signal at a lower level of quality to compensate for limited bandwidth and/or decoder computing resources. In one case, progressive decoding may be used such that each decoder device decodes as high a level of quality as constraints allow. This may also allow for graceful fallback, e.g. if bandwidth or available resources vary during transmission.

The encoder device 108 may receive data at multiple resolutions and prepare multiple encoded data signals based on this. In one case, different received resolutions (e.g. different resolutions of a common frame) may be used instead of downsampling a signal.

The decoder device 110 may output data that allows an image having multiple different levels of quality to be displayed to a viewer. The image may have one or more relatively high quality regions and one or more relatively low quality regions. The image may have one or more intermediate quality regions. The relatively high quality region may correspond to a region of the image the viewer is looking at or is likely to be looking at. The relatively low quality region may be a region of the image the viewer is not looking at or is unlikely to be looking at. The viewer may thus have an option to view either the whole of the data or a portion of the data at different levels of quality, depending on one or more of current processing constraints and/or regions of interest. This may be useful for medical telepresence where it may be desired to regularly zoom in and out and pan around a wide area of view. Similar requirements may be present for military and/or civil engineering uses.

The present examples may cover one or more of encoders and decoders.

Regions of Interest

There are various different ways to determine which region or regions of an image a viewer is looking at or is likely to look at. For example, the viewer may indicate one or more regions of interest themselves, using a pointing device for instance. An eye tracker may be used to determine one or more fixation points of the viewer. A fixation point may be determined based on the centre of the retina of the eye of the viewer. The first and/or second apparatus 102, 104 may be able to determine a likely region of interest in the image. For example, the first and/or second apparatus 102, 104 may be able to predict a likely region of interest based on historic regions of interest and/or knowledge of the data signal.

In one possible arrangement of a data signal processing system, the decoder device is configured to provide feedback to the encoder device on a region of interest in an image. For example, the region of interest in the image may correspond to the field of view of a viewer and/or one or more fixation points of the viewer. The encoder device could then generate and transmit to the decoder device an encoded version of the image with the region of interest at a relatively high level of quality and other regions of the image at one or more lower levels of quality. The decoder device could decode the received encoded data and output decoded data so that such an image having the characteristics set by the encoder device can be displayed to the viewer. In this case, the size of the encoded data transmitted by the encoder device to the decoder device could be made smaller than the size of a corresponding version of the image where all of the image is at the same, high level of quality. This means that less data could be transmitted from the encoder device to the decoder device over the data communication network.

Although reducing the amount of data transmitted over a data communication network may be desirable in some cases, the possible arrangement described above involves the decoder device feeding back information on the region of interest to the encoder device to allow the encoder device to encode the various regions of the image at the desired levels of quality. This may involve establishing and maintaining a dedicated feedback channel for example, and relies on data connectivity between the encoder device and the decoder device in order to function. In addition, feeding back data in this way may increase the amount of time required to display an image as the decoder device provides the feedback information to the encoder device, the encoder device encodes the image based on the feedback, the encoder device transmits the encoded image to the decoder device and the decoder device decodes the image for display to the viewer. Such a delay may be unacceptable or undesirable in some situations, for example where substantially real-time image processing is desired. This may be relevant in virtual reality applications, where noticeable delays or lags may detract from user experience.

Further, in the possible arrangement described above, the decoder device has limited control over which regions of the image would be displayed at the different levels of quality. The encoder device would already have set the levels of quality of the various regions of the image based on the feedback from the decoder device by the time the decoder device receives the encoded image, limiting the amount of control the encoder device has on how the image is displayed. This may impact the decoder device and/or the second apparatus, for example where the decoder device and/or the second apparatus has limited capacity, battery life, processing power etc.

In contrast, as described herein, the decoder device 110 is configured to receive data useable to generate data for representing a data signal, for example an image data signal and/or video data signal, at a first level of quality. Data for representing a data signal is data useable to represent the data signal. The decoder device 110 is configured to receive enhancement data useable to generate data for representing the data signal at a second, higher level of quality based on the representation of the data signal at the first level of quality.

The decoder device 110 is configured to generate data for representing a target region of the data signal at a target level of quality using a selected portion of the enhancement data. The target region of the data signal may correspond to where the viewer is looking or is likely to be looking.

Only some, rather than all, of the enhancement data is selected. The selected portion of the enhancement data is associated with the target region of the data signal. The decoder device 110 may select the portion of the enhancement data itself and/or may determine the selected portion of the enhancement data based on receiving data comprising an identification of the selected portion of the enhancement data. The data comprising the identification of the selected portion of the enhancement data may be received from one or more further entities. The one or more further entities may comprise, for example, the encoder device 108. The decoder device 110 may determine the selected portion of the enhancement data to be used based on the received data.

The target level of quality is higher than the first level of quality. The target level of quality may be the same as the second level of quality. The target level of quality may instead be between the first level of quality and the second level of quality.

The decoder device 110 may identify the target region of the data signal itself and/or may determine the target region of the data signal based on receiving data comprising an identification of the target region. The data comprising the identification of the target region may be received from one or more further entities. The one or more further entities may comprise, for example, the encoder device 108.

The decoder device 110 is configured to generate data for representing a further region of the data signal at a level of quality lower than the target level of quality. Where the data signal is an image data signal and/or video data signal, the further region may correspond to a region of the image and/or video the viewer is not looking at or is unlikely to look at.

The level of quality associated with the further region may be the first level of quality. Alternatively, the level of quality associated with the further region may be between the first level of quality and the target level of quality.

In some examples, where the level of quality associated with the further region is between the first level of quality and the target level of quality, the decoder device 110 is configured to generate the data for representing the further region using a selected further portion of the enhancement data. The decoder device 110 may select the further portion of the enhancement data itself and/or may determine the selected further portion of the enhancement data based on receiving data comprising an identification of the selected further portion of the enhancement data.

As such, the decoder device 110 receives a fully encoded data signal, for example from the encoder device 108. The data signal is fully encoded in that the decoder device 110 could use the fully encoded data signal to generate a version of the data signal where all regions are at the high level of quality. Instead, however, the decoder device 110 decodes part of the fully encoded data signal at a first level of quality and another part at a second, higher level of quality. In some examples, the decoder device 110 generates data for representing the entire data signal at the first level of quality and data for representing only a region of the data signal at the higher level of quality. The decoder device 110 may use part of the data for representing the entire data signal at the first level of quality to generate the data for representing only the region of the data signal at the higher level of quality.

These examples differ from the possible arrangement described above in which the encoder device does not provide a fully encoded image and/or video data signal, but selects which parts of the image and/or video stream are to be provided at the different quality levels based on the feedback from the decoder device. In contrast, in the examples described herein, the decoder device 110 has more control over which regions of the image and/or video are decoded at particular levels of quality. The decoder device 110 may be able to use feedback information based on where in the image and/or video the viewer is looking to determine the target region and further regions of the image instead of feeding such information back to the encoder device 108 over the data communications network 106. Such feedback information may comprise data identifying the target region and/or further region and/or may comprise data the decoder device 110 can use to determine the target region and/or further region itself.

Further, the decoder device 110 can selectively optimise the resources to use for decoding. This may result in savings in battery usage. In addition, the decoder device 110 may not need to provide any feedback at all to the encoder device 108. Further still, it may not be necessary to modify any functionality at the encoder device 108 if the encoder device 108 is configured to transmit the fully encoded data signal.

A trade-off of the encoder device 108 transmitting the fully encoded data signal is that more data may be transmitted between the encoder device 108 and the decoder device 110 via the data communications network 106 than would be the case if the encoder device 108 selectively encoded the data signal at predetermined different levels of quality based on feedback from the decoder device 110.

Hierarchical Data Signal Processing

Figure 2:
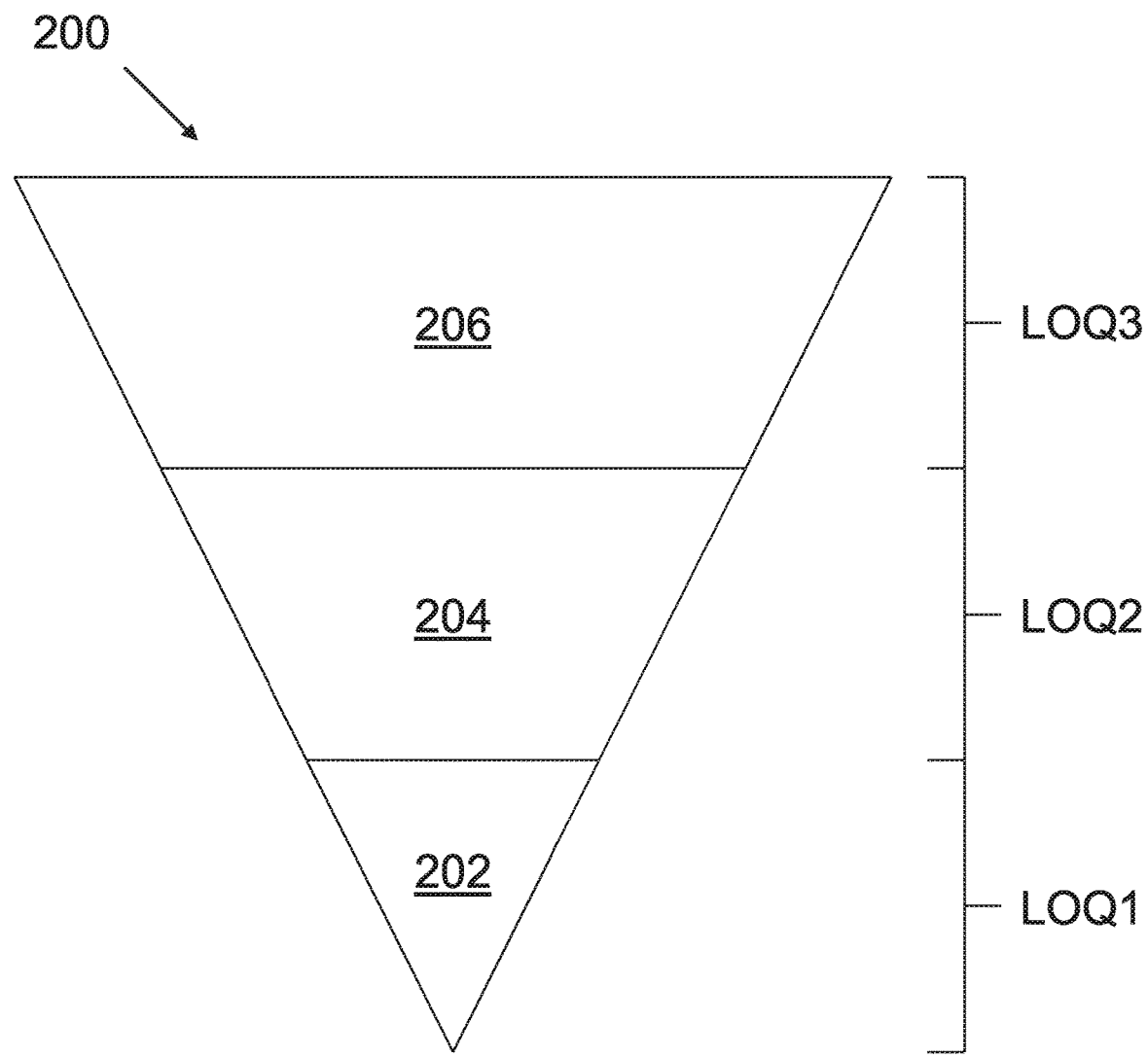
FIG. 2 shows a schematic diagram of an example of a hierarchical data signal processing arrangement.

Referring to FIG. 2, there is shown schematically an example of a hierarchical data signal processing arrangement 200.

The hierarchical data signal processing arrangement 200 represents multiple different levels of quality. The levels of quality may relate to different levels of quality of data associated with the data signal. A factor that can be used to determine quality of image and/or video data is resolution. A higher resolution corresponds to a higher level of quality. The resolution may be spatial and/or temporal. Other factors that can be used to determine quality of image and/or video data include, but are not limited to, a level of quantization of the data, a level of frequency filtering of the data, peak signal-to-noise ratio of the data, a structural similarity (SSIM) index, etc.

In this example, the hierarchical data signal processing arrangement 200 has three different layers (or 'levels'), namely a first layer 202, a second layer 204 and a third layer 206. The hierarchical data signal processing arrangement could however have a different number of layers. The first layer 202 may be considered to be a base layer in that it represents a base level of quality and the second and third layers 204, 206 may be considered to be enhancement layers in that they represent enhancements in terms of quality over that associated with the base layer. The first layer 202 corresponds to a first level of quality LOQ1. The second layer 204 corresponds to a second level of quality LOQ2. The second level of quality LOQ2 is higher than the first level of quality LOQ1. The third layer 206 corresponds to a third level of quality LOQ2. The third level of quality LOQ3 is higher than the second level of quality LOQ2. The second level of quality LOQ2 is between (or 'intermediate') the first level of quality LOQ1 and the third level of quality LOQ3.

In some examples, the hierarchical data signal processing arrangement 200 represents multiple different levels of quality of video data. For example, the first layer 202 may correspond to standard definition (SD) quality video, the second layer 204 may correspond to high definition (HD) quality video and the third layer 206 may correspond to ultra-high definition (UHD) video for example. Different combinations of different resolutions may be used, e.g. SD and UHD, HD and UHD, or SD, HD and UHD.

In this example, each of the layers 202, 204, 206 is associated with respective enhancement data. Enhancement data may be used to generate data, such as image and/or video data, at a level of quality associated with the respective layer as will be described in more detail below.

Figure 12:
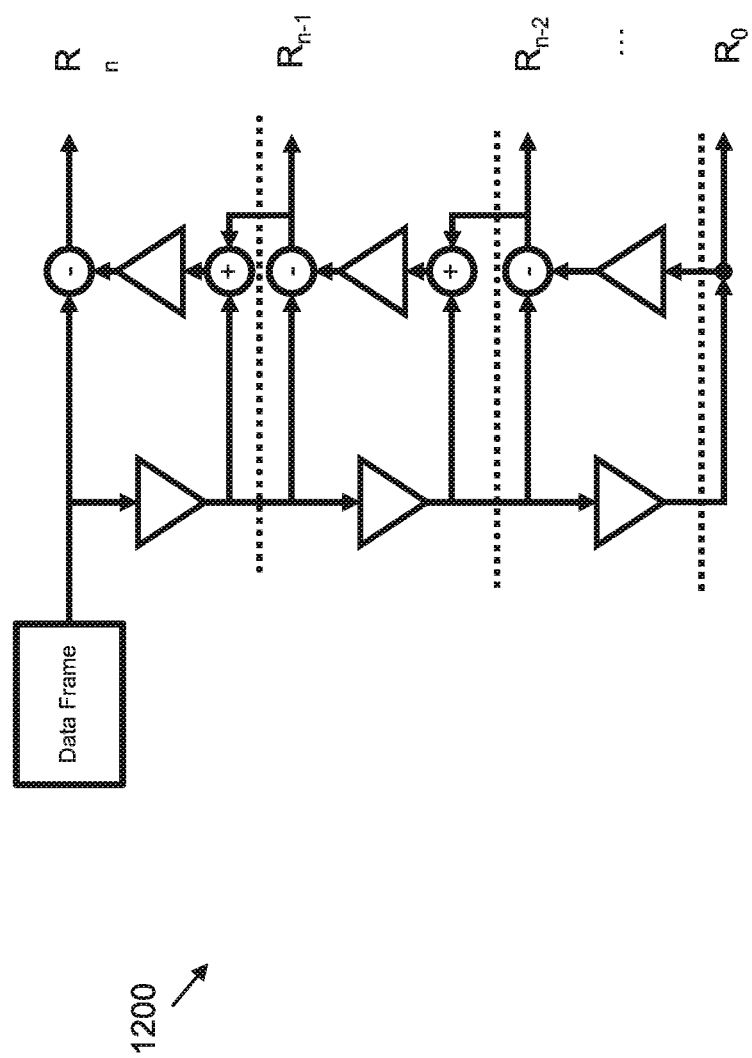
FIG. 12 shows an example encoder for a hierarchical encoding scheme.
Figure 13:
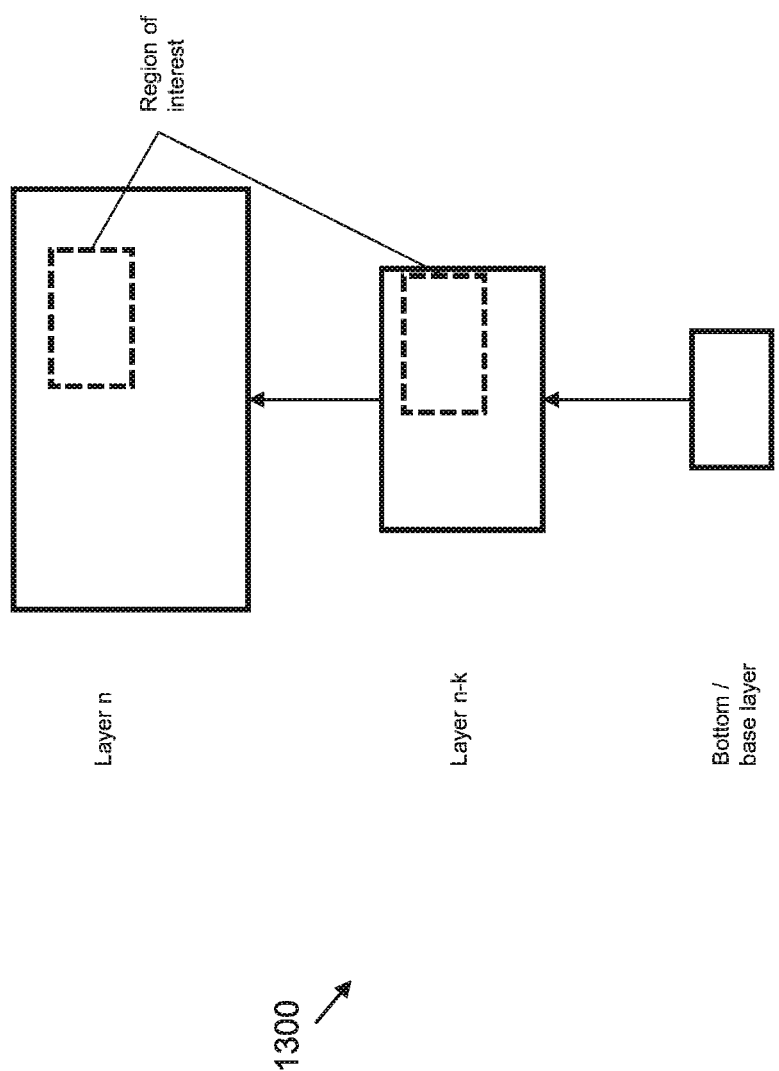
FIG. 13 shows different levels of quality and different regions of interest.

FIG. 12 also shows how a data plane of a data frame is received and is successively downsampled to generate a plurality of layers (0 to n are shown). The base layer may be a lowest layer and may represent an output of a last downsampling step (or a difference between that layer and a scalar offset). Higher layers are represented as residual data where an upsampled version of a lower layer is compared with an input (non-upsampled) version (e.g. following downsampling for layer $R_{n-1}$ as shown), e.g. by subtracting a reconstructed upsampled version of a lower layer from the input version. Residual data allows efficient representation of the data frames, and may be particularly useful for sparse data where there may only be a few values within the residual data. On a decoding side the process may be reversed on receipt of encoded streams derived from $R_0$ to $R_n$ representing the layers. FIG. 2 does not show encoding operations, which may comprise transforming, quantising and entropy encoding residual data.

Some examples of hierarchical coding are set out in the SMPTE VC-6 standard, and the MPEG-5, Part-2, LCEVC standard (the specifications for both standards, including working drafts, being incorporated herein by reference). Additional descriptions of hierarchical coding may be found in one or more of U.S. Pat. No. 8,977,065, filed on Jul. 21, 2011, entitled "Inheritance in a tiered signal quality hierarchy," the contents of which are hereby incorporated by reference in their entirety; U.S. Pat. No. 8,948,248, filed on Jul. 21, 2011, entitled "Tiered signal decoding and signal reconstruction," the contents of which are hereby incorporated by reference in their entirety; U.S. Pat. No. 8,711,943, filed on Jul. 21, 2011, entitled "Signal processing and tiered signal encoding," the contents of which are hereby incorporated by reference in their entirety; U.S. Pat. No. 9,129,411, filed on Jul. 21, 2011, entitled "Upsampling in a tiered signal quality hierarchy," the contents of which are hereby incorporated by reference in their entirety; and U.S. Pat. No. 8,531,321, filed on Jul. 21, 2011, entitled "Signal processing and inheritance in a tiered signal quality hierarchy," the contents of which are hereby incorporated by reference in their entirety.

Figure 3:
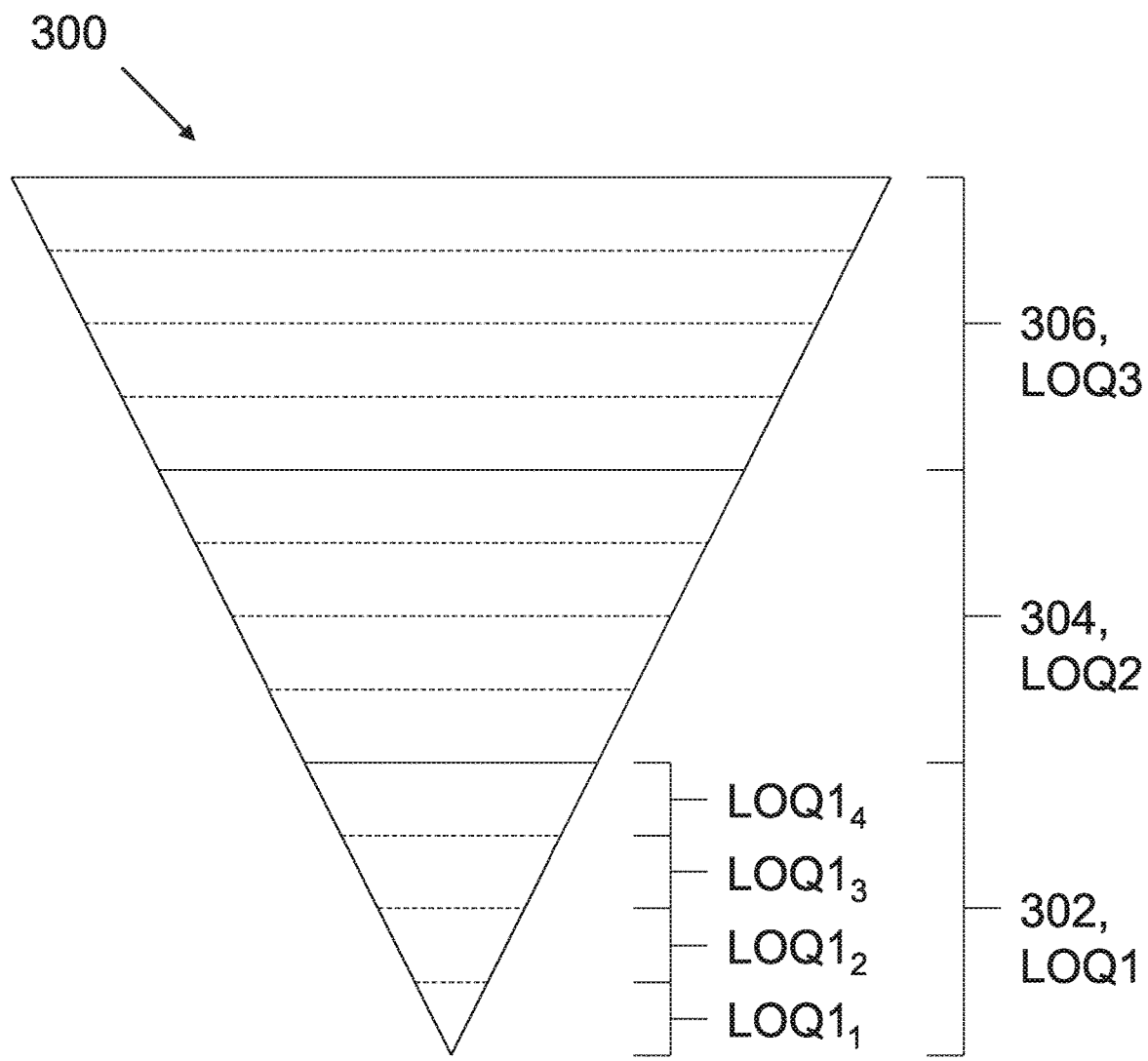
FIG. 3 shows a schematic diagram of another example of a hierarchical data signal processing arrangement.

Referring to FIG. 3, there is shown schematically an optional variation of a hierarchical data signal processing arrangement 300. This may only be used for certain implementations and may not be used for typical implementations.

The hierarchical data signal processing arrangement 300 shown in FIG. 3 is similar to the hierarchical data signal processing arrangement 200 shown in FIG. 2 in that it includes three layers 302, 304, 306. In this example, each of the layers 302, 304, 306 includes a set of sub-layers (or 'sub-levels'). In this specific example, each of the layers includes four sub-layers.

The first layer 302 is associated with a first level of quality LOQ1. Each of the sub-layers of the first layer 302 is associated with a respective level of quality. A first sub-layer of the first layer 302 is associated with level of quality $LOQ1_1$, a second sub-layer of the first layer 302 is associated with level of quality $LOQ1_2$, a third sub-layer of the first layer 302 is associated with level of quality $LOQ1_3$ and a fourth sub-layer of the first layer 302 is associated with level of quality LOQ14. Similarly, the second layer 304 is associated with a second level of quality LOQ2, the third layer 306 is associated with a third level of quality LOQ3 and the sub-layers of the second and third layers 304, 306 are associated with respective, increasing levels of quality. The level of quality associated with layers and sub-layers higher in the hierarchical data signal processing arrangement 300 is higher than the level of quality associated with layers and sub-layers lower in the hierarchical data signal processing arrangement 300. As such, the level of quality increases from the bottom to the top of the hierarchical data signal processing arrangement 300.

Some or all of the layers 302, 304, 306 could have a number of sub-layers other than four. Some of all of the layers 302, 304, 306 could have a different number of sub-layers than each other. Some of the layers 302, 304, 306 may not have any sub-layers.

In this example, each of the sub-layers is associated with respective enhancement data. Enhancement data may be used to generate data, such as image and/or video data, at a level of quality associated with the respective sub-layer, as will be described in more detail below.

The hierarchical data signal processing arrangement 300 therefore comprises a first layer having a first set of sub-layers and a second layer having a second set of sub-layers. Each of the sub-layers is associated with a respective level of quality and is associated with respective enhancement data. Using a hierarchical data signal processing arrangement such as the hierarchical data signal processing arrangement 300 may allow some devices to reconstruct at a specific layer, for example LOQ3, but only using say the first two sub-layers, $LOQ3_1$ and $LOQ3_2$, of that layer. This may be for efficiency, battery saving or limited capacity purposes. Using only some sub-layers may be considered to be partial reconstruction. Other devices may use all four of the sub-layers in LOQ3, namely $LOQ3i$, $LOQ3_2$, $LOQ3_3$ and LOQ34, and reconstruct the signal completely. Using all of the sub-layers may be considered to be full reconstruction. The reader is referred to UK patent application no. GB1603727.7, which describes a hierarchical arrangement in more detail. The entire contents of GB1603727.7 are incorporated herein by reference.

Hierarchical Storage Management

In one set of examples, an encoder as described herein may alternatively (or additionally) generate one or more data files as well as one or more data streams. These may be stored in non-volatile storage for later viewing (e.g. as part of an audit or for education and training). In certain cases, a Hierarchical Storage Management (HSM) system may be used to store data in the layer format discussed above. These HSM systems can leverage the hierarchical nature of approaches such as SMPTE VC-6, by storing different resolutions in different files. HSM systems may also be adapted to manage content in an effective manner, e.g. with the lower resolution and/or most frequently accessed resolutions stored on the most immediate storage so as to allow for fast delivery. This may be especially advantageous as the lower levels or layers may be reasonably small, and so may be quickly and easily received by viewing users, where the user may then use the quickly delivered low-resolution layer or layers to select a region of interest (e.g., including for panning or zooming), and higher resolution layers, which may take up more data, are delivered for only the region of interest, which is a smaller spatial area (e.g. than a full field of view) and so may also be quickly delivered.

Where multiple image/video sources are being transferred, typically only one is viewed at full resolution. Therefore, when encoding multiple sources, all are encoded at full resolution for archival, but only the resolutions required to be transferred are transferred.

Additionally, where the transfer bandwidth is constrained systems may reduce the resolution being transferred, while storing the full resolution. Then only transferring the higher resolutions on demand or when the link has spare capacity.

Viewing Target Regions

Figure 4:
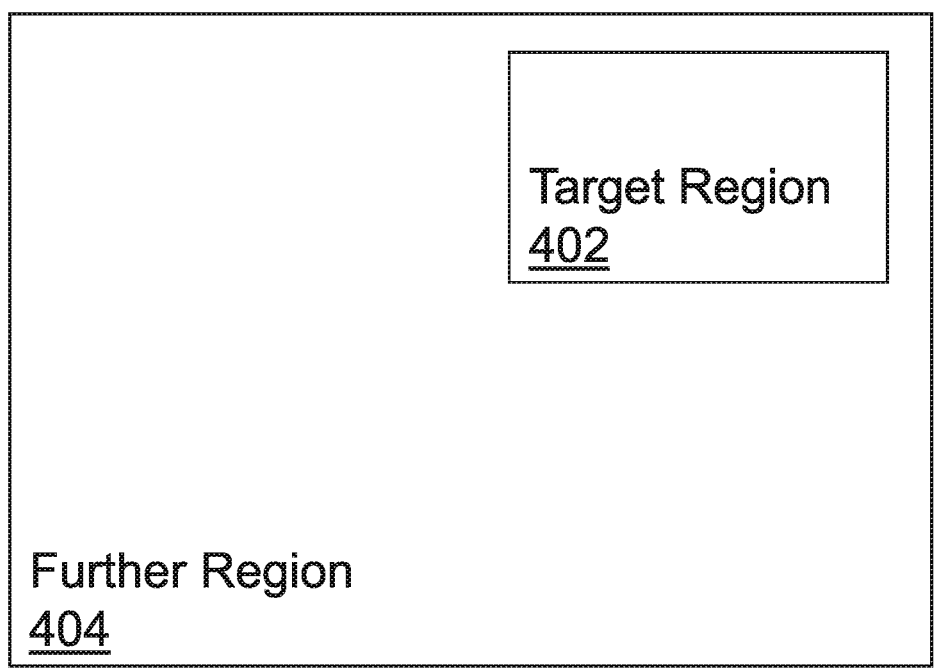
FIG. 4 shows schematically an example of an image.

Referring to FIG. 4, there is shown an example of an image 400. The image 400 may for example be obtained from video data. The image may depict a scene. For example, the image may depict a medical procedure, a remote military operation, a frame of a video witness statement or a view of an augmented reality bridge inspection. The examples described herein may be applied to, amongst others, telemedicine, geographic information systems (GIS), insurance, military reconnaissance, surveillance, hazardous area engineering and exploration. Many different uses in many different fields of application are envisaged.

The image 400 includes a target region 402. The target region 402 is a region of interest in relation to the image 400. The target region 402 may correspond to a region of the image 400 the viewer is currently looking at and/or is likely to look at. The target region 402 is of interest in relation to the image 400 as the viewer is likely to be particularly perceptive to the level of quality of the image in the target region 402. In the example of the image 400 depicting a medical procedure, such as surgery, the target region 402 may correspond to a region of the image 400 including an organ being operated on. Although the target region 402 is depicted as being rectangular in FIG. 4 it could take a different form. For example, it could correspond to the outline of an item of interest in the image, for example the outline of the organ.

An image may include one or more target regions. For example, an image may include multiple target regions associated with respective different viewers where multiple viewers are viewing the image at the same time.

The image 400 includes a further region 404. The further region 404 may correspond to a region of the image 400 the viewer is currently not looking at and/or is unlikely to look at. The viewer is likely to be less perceptive to the level of quality of the image in the further region 404. In the example of the image 400 depicting a medical procedure, the further region 404 may correspond to a region of the image 400 including the whole patient body or general field of view. The further region 404 surrounds the target region 402. An image may include one or more such further regions 404.

Figure 5:
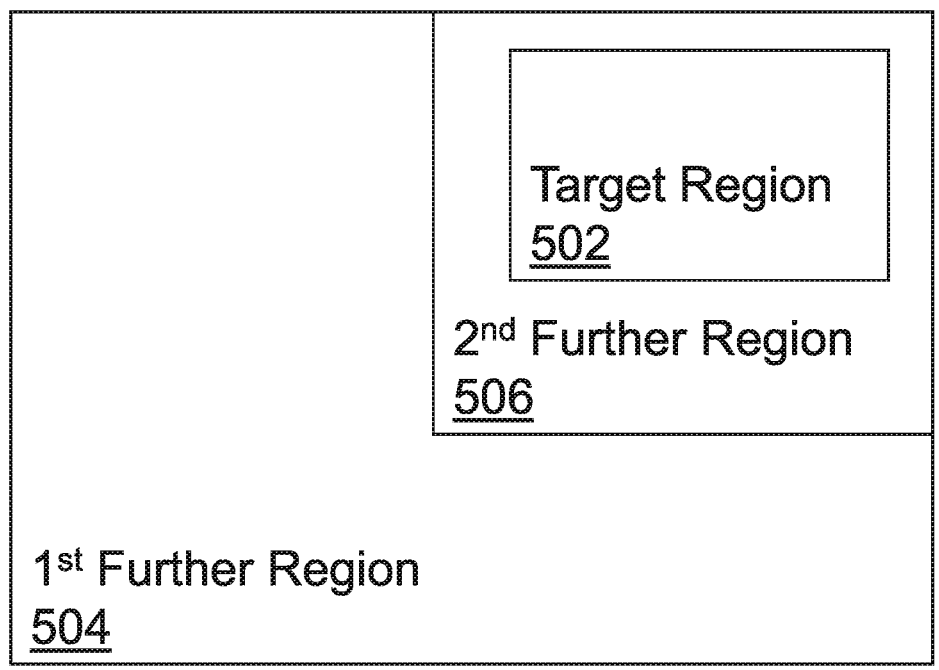
FIG. 5 shows schematically another example of an image.

Referring to FIG. 5, there is shown an example of an image 500.

The image 500 includes a target region 502, a first further region 504 and a second further region 506. In this example, the target region 502 is associated with a high level of quality, the first further region 504 is associated with a low level of quality and the second further region 506 is associated with an intermediate level of quality. The second further region 506 surrounds the target region 502. The first further region 504 partly surrounds both the target region 502 and the second further region 506.

In both the examples of FIGS. 4 and 5, only the target region 402 or 502 may need to be streamed and/or decoded. For example, if all viewers are viewing the same region of interest, only that region of interest needs to be encoded and stream. In certain cases, an encoder may encode and stream all portions, but decoder devices may selectively receive the streams and/or decode the streams. For example, to provide a stream locally of a cut-out portion of an object or field of view only the cut-out needs to be decoded. If the region of interest is served to a consumer device (e.g. being streamed on the Internet as well as recipients on a local network), there no scaling may be required to re-encode this for onward delivery, instead just the additional layers that represent the detail for the target region 402 and 502 need be delivered.

In this scenario, where the network is congested a user can define an area of interest for higher priority, so that the quality of priority information is still maintained while the context information is still presented at a lower resolution. For example, during critical real-time operations, such as surgery and military operations, it may be desired to maintain a particular region including a target at a high quality and other areas may gracefully degrade in quality if network congestion or resource issues are experienced. In this example, and even examples where the whole field of view is encoded and decoded, progressive decoding of the hierarchy of layers allows as much information as is available to be provided, as soon as possible.

Figure 16:
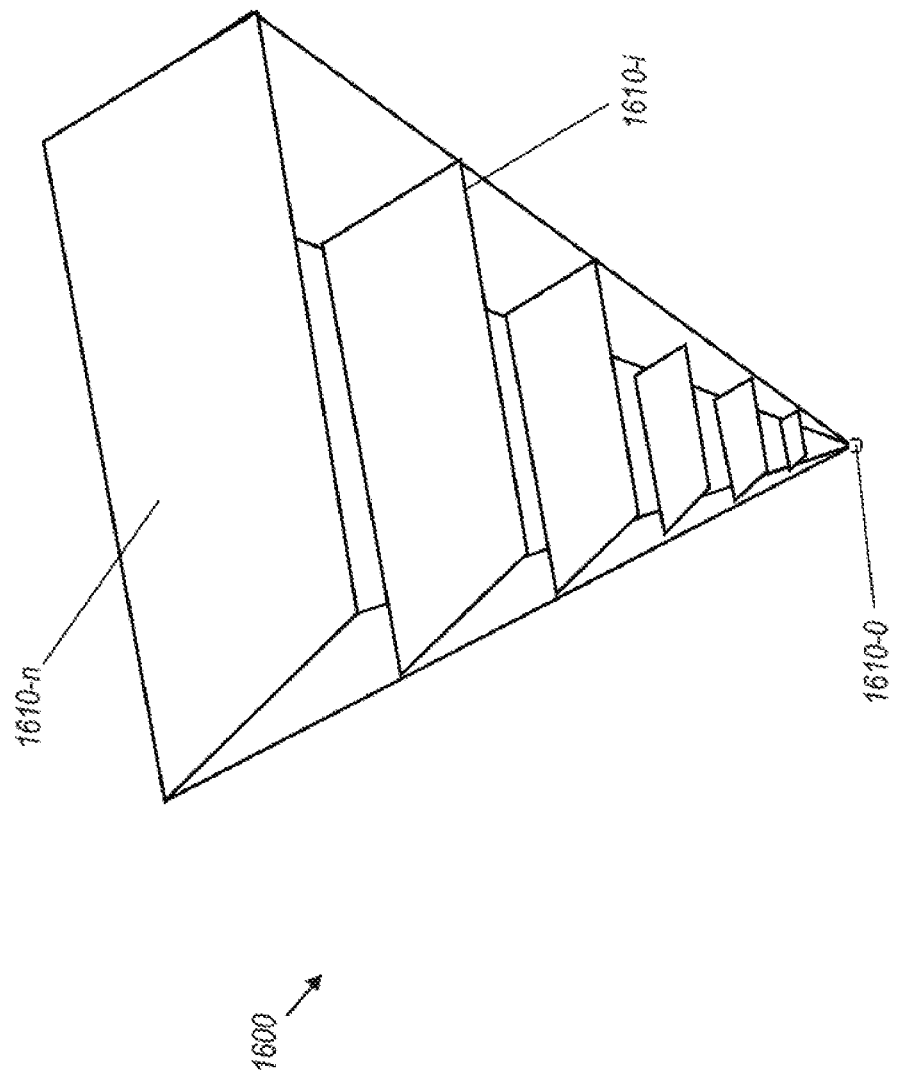
FIG. 16 is a schematic illustration showing a number of levels of quality within a first example hierarchical coding scheme.
Figure 17:
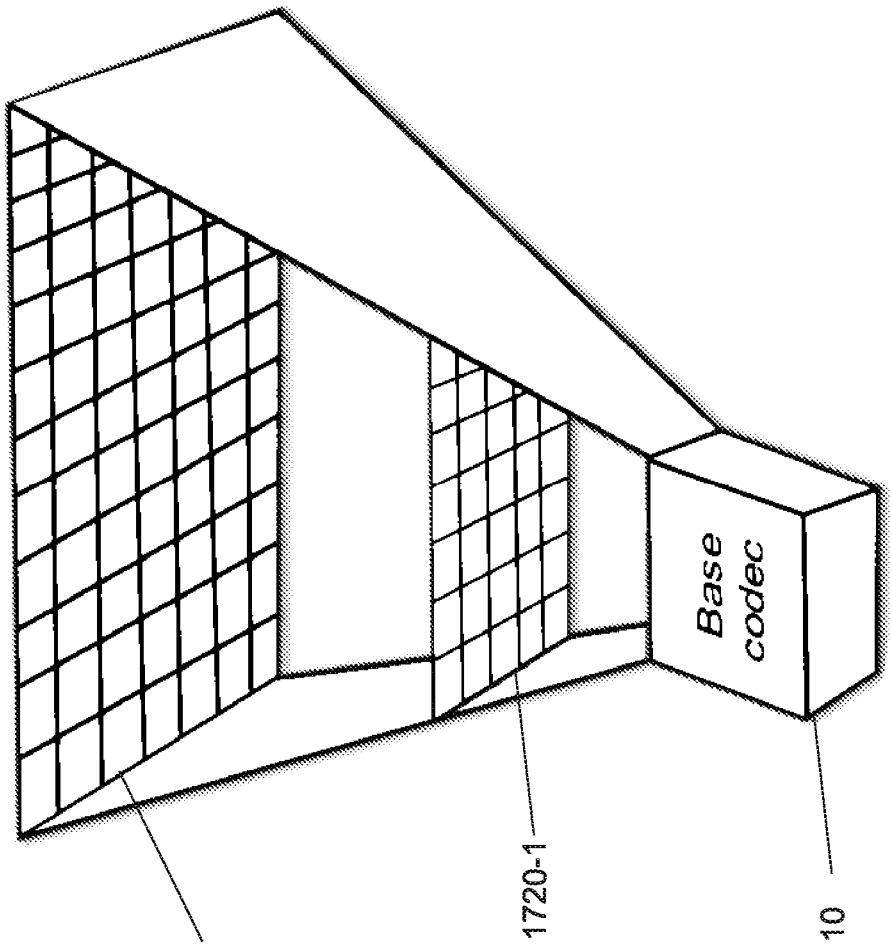
FIG. 17 is a schematic illustration showing a number of levels of quality within a second example hierarchical coding scheme.

In certain examples, in very constrained or public networks, streaming may be configured to use MPEG-5 Part 2 (LCEVC), as an alternative to the full-codec approach of SMPTE VC-6. For example, hierarchical encoding according to SMPTE VC-6 may be preferred for higher quality local transmissions where requirements are similar to video production (e.g. neighbouring rooms in a hospital or education establishment), but MPEG-5 Part 2 may be preferred for wider streaming over secure or unsecure networks (e.g. streaming over the Internet). The approach of SMPTE VC-6 is further shown in FIG. 16, where there are a plurality of layers of quality going down to a lowest layer of quality, where all layers are encoded with a common codec. The approach of MPEG-5, Part 2, is shown in FIG. 17, wherein there is a base codec and one or more layers that are encoded using a separate enhancement codec. When bandwidth is limited, MPEG-5, Part 2 may degrade to just use a base stream as generated by a base or legacy codec. This may be at a lower resolution to a full desired stream, wherein the enhancement levels or layers may allow a higher resolution. Instead of needing the base codec to encode 100% of the initial resolution, it may only need to encode 25% of the initial resolution, thus reducing the load on the base codec and allowing base encoded frames to be received even if resources are limited. If the enhancement codec is more efficient than the base codec, MPEG-5 Part 2 may allow a legacy codec to continue operating within its comfort zone while the quality at the higher resolution remains unaffected.

Example Data

Figure 6:
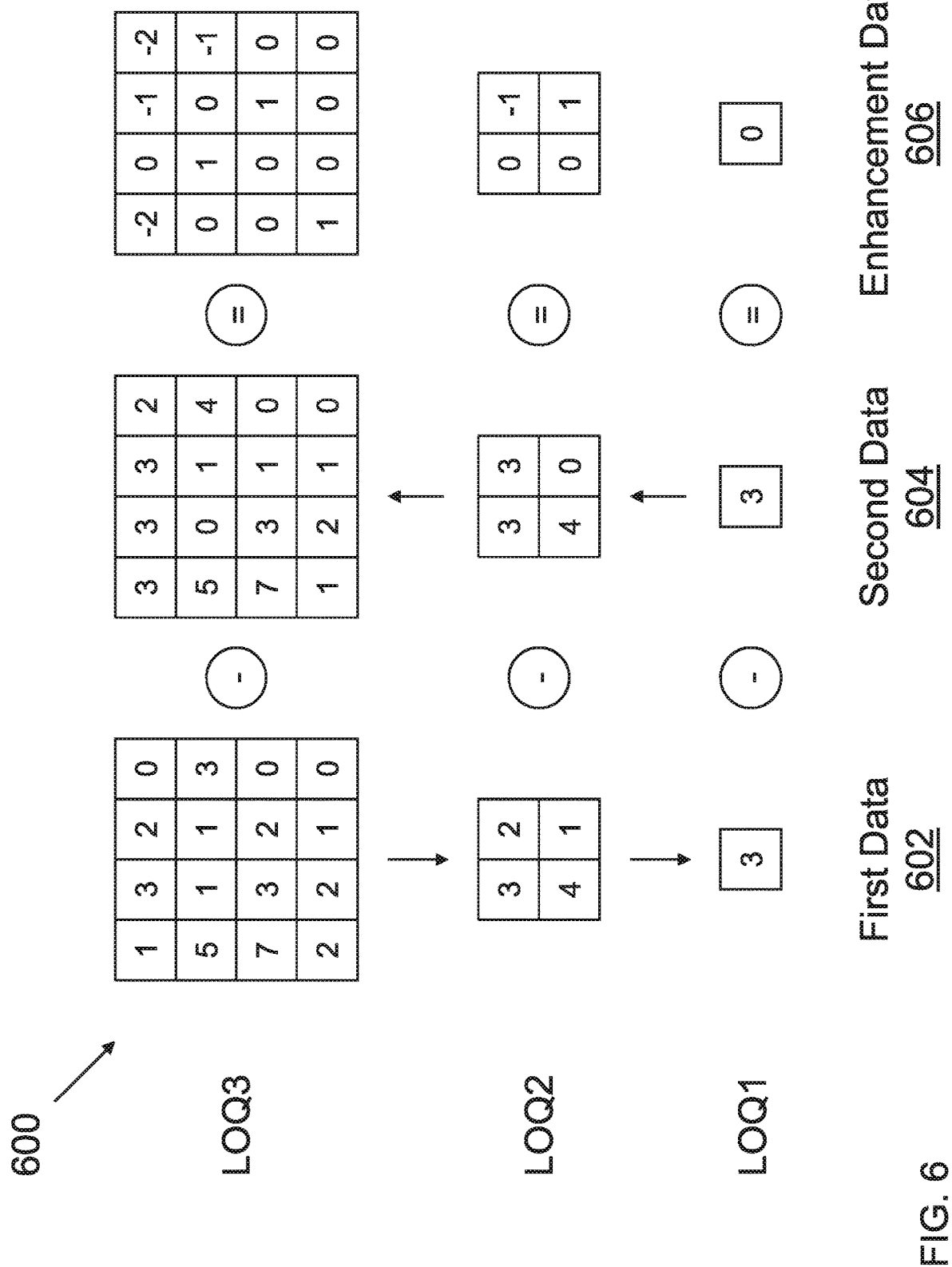
FIG. 6 shows schematically an example of data useable in a data signal processing system.

Referring to FIG. 6, there is shown example data 600 associated with the data signal processing system 100. In this example, the data 600 is obtained and/or generated by the encoder device 108. In this example, the data 600 is related to data for representing an image at different levels of quality.

The data 600 includes first data 602. In this example, the first data 602 corresponds to data for representing the image at different levels of quality, from a highest level of quality LOQ3 to a lowest level of quality LOQ1. For convenience, example values have been included in the data for representing the image at the different levels in FIG. 6, it being understood that other values could be used. The values in the data for representing the image may for example correspond to pixel values.

In this example, the data for representing the image at LOQ3 in the first data 602 corresponds to an original version of the image. In other words, in this example, the data for representing the image at LOQ3 in the first data 602 is the same as the original version of the image. The resolution of the data for representing the image at LOQ3 is 4×4. It will be appreciated that, in reality, the resolution of the data for representing the image may be much higher than 4×4. For example, the resolution may be tens, hundreds or thousands of elements by tens, hundreds or thousands of image elements. The resolution may, for example, be 1920×540.

The data for representing the image at LOQ3 in the first data 602 is downsampled to generate the data for representing the image at LOQ2 in the first data 602. The resolution of the data for representing the image at LOQ2 in the first data 602 is 2×2. In this example, the downsampling operation averages four neighbouring values in the data for representing the image at LOQ3 in the first data 602 and rounds the average value to the nearest integer. For example, with reference to FIG. 6, the bottom-left values (namely 7, 3, 2, 2) in LOQ3 have been averaged to produce the bottom-left value in LOQ2 (i.e., 4), and the values in LOQ2 (i.e., 3, 2, 4, 1) have been averaged to produce the value in LOQ1 (i.e., 3). It will be appreciated that other techniques may be used for generating lower quality representations of an image however. In particular, in some examples, the data for representing an image at a lower level of quality has the same resolution as the data for representing the image at a higher level of quality. The difference in the level of quality may in such examples relate to an amount of enhancement or correction applied to the data for representing the image.

The data for representing the image at LOQ2 in the first data 602 is downsampled to generate data for representing the image at LOQ1 in the first data 602. In this example, the downsampling operation averages the four values in the data for representing the image at LOQ2 in the first data 602 and rounds the average value to the nearest integer. The resolution of the data for representing of the image at LOQ1 in the first data 602 is 1×1. Although, in this example, the resolution of the data for representing the image at LOQ1 in the first data 602 is 1×1, in reality the downsampling operations may not reduce the resolution to 1×1. For example, the resolution of the data for representing the image at LOQ1 in the first data 602 may be tens, hundreds or thousands of elements by tens, hundreds or thousands of image elements.

The data 600 also includes second data 604. In this example, the second data 604 corresponds to different representations of the image at levels of quality LOQ1, LOQ2 and LOQ3, from a lowest level of quality LOQ1 to a highest level of quality LOQ3.

In this example, the data for representing the image at LOQ1 in the second data 604 is the same as the data for representing the image at LOQ1 in the first data 602. In other examples, the data for representing the image at LOQ1 in the second data 604 is different from the data for representing the image at LOQ1 in the first data 602. The resolution of the data for representing the image at LOQ1 in the second data 604 is 1×1.

The data for representing the image at LOQ1 in the second data 604 is upsampled to generate the data for representing the image at LOQ2 in the second data 604. In this example, the upsampling operation comprises a Nearest Neighbour operation, such as Nearest Neighbour Interpolation. It will be appreciated that other techniques may be used for generating higher quality representations of an image however. The resolution of the data for representing the image at LOQ2 in the second data 604 is 2×2.

The data for representing the image at LOQ2 in the second data 604 is upsampled to generate data for representing the image at LOQ3 in the second data 604. In this example, the upsampling operation comprises a Nearest Neighbour operation, such as Nearest Neighbour Interpolation. The resolution of the data for representing the image at LOQ3 in the second data 604 is 4×4.

The upsampling and downsampling operations result in differences between the values in the data for representing the image at a given level of quality in the first data 602 and the second data 604. This is because the upsampling and downsampling operations are asymmetrical. For example, the top right value in the data for representing the image at LOQ2 in the first data 602 is "2" whereas it is "3" in the data for representing the image at LOQ2 in the second data 604.

In this example, enhancement data 606 is generated by subtracting a value in the data for representing the image at a given level of quality in the second data 604 from a corresponding value in the data for representing the image at the given level of quality in the first data 602. For example, the top right value in the enhancement data 606 at LOQ2 is "−1", is obtained by subtracting the top right value "3" in the data for representing the image at LOQ2 in the second data 604 from the top right value "2" in the data for representing the image at LOQ2 in the first data 602. In other examples, the enhancement data 606 is generated based on another relationship between a value in the data for representing the image at a given level of quality in the second data 604 and a corresponding value in the data for representing the image at the given level of quality in the first data 602.

In this example, the encoder device 108 transmits the data for representing the image at LOQ1 in the second data 604 and all of the enhancement data 606 to the decoder device 110. The decoder device 110 is then able to recover all of the representations of the image in the first data 602.

Figure 7:
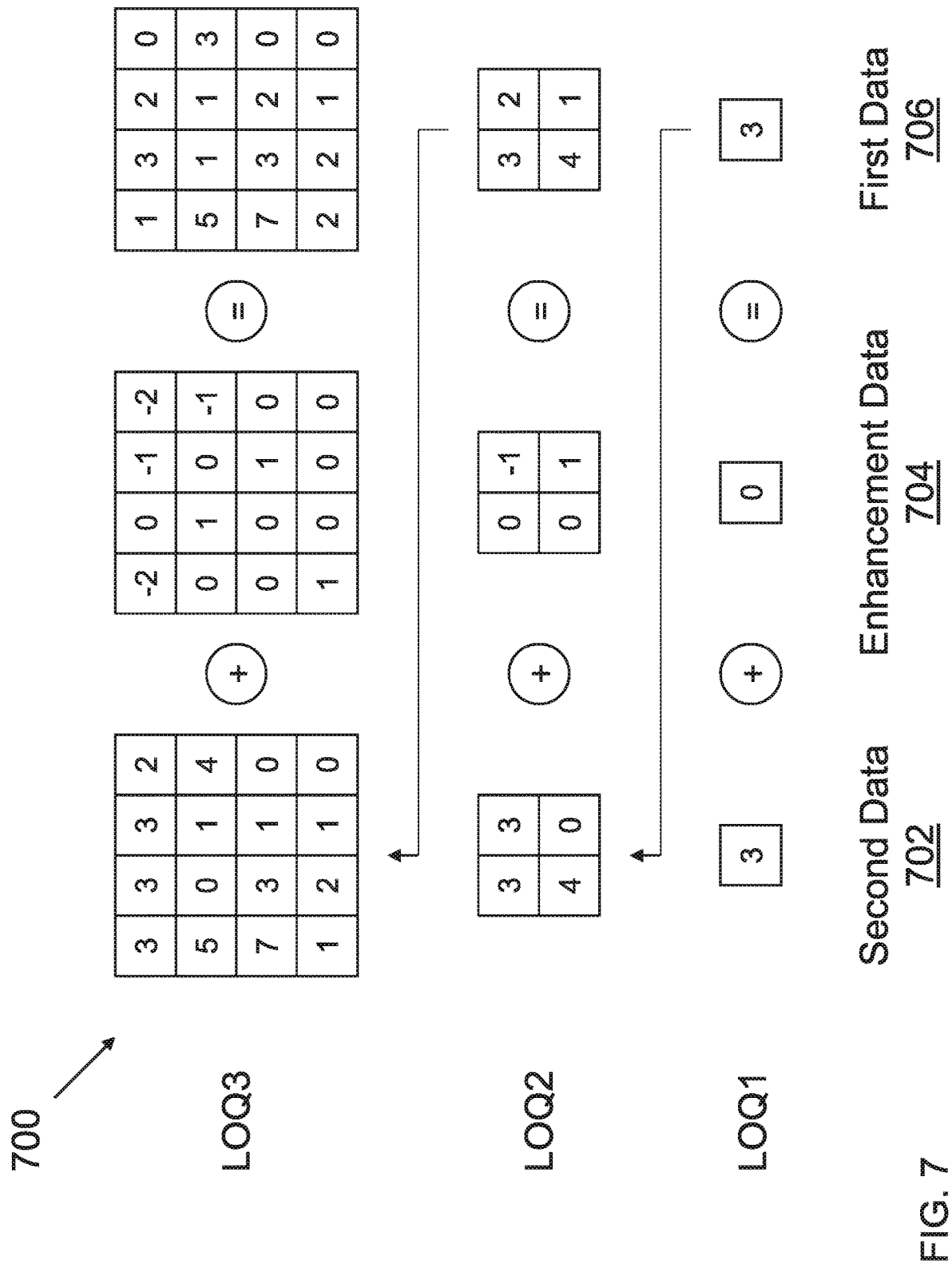
FIG. 7 shows schematically another example of data useable in a data signal processing system.

Referring to FIG. 7, there is shown example data 700 associated with the data signal processing system 100. In this example, the data 700 is obtained by the decoder device 110. In this example, the data 700 is for representing an image at different levels of quality.

The example data 700 includes second data 702, enhancement data 704 and first data 706. The second data 702 is the same as the second data 604 described above with reference to FIG. 6. The enhancement data 704 is the same as the enhancement data 606 described above with reference to FIG. 6. The first data 706 is the same as the first data 602 described above with reference to FIG. 6.

It can be seen from FIG. 7 that the first data 706 can be recovered using the data for representing the image at LOQ1 in the second data 702 and the enhancement data 704 by reversing the operations performed by the encoder device 108 described above with reference to FIG. 6. In particular, the decoder device 110 uses the data for representing the image at LOQ1 in the second data 702 and the enhancement data 704 at LOQ1 to generate the data for representing the image at LOQ1 in the first data 706. The decoder device 110 then upsamples the data for representing the image at LOQ1 in the first data 706 to generate data for representing the image at LOQ2 in the second data 702 and uses the enhancement data 704 at LOQ2 along with the data for representing the image at LOQ2 in the second data 702 to generate the data for representing the image at LOQ3 in the first data 706. The decoder device 110 then upsamples the data for representing the image at LOQ3 in the first data 706 to generate the data for representing the image at LOQ3 in the second data 702 and uses the enhancement data 704 at LOQ3 along with the data for representing the image at LOQ3 in the second data 702 to generate the data for representing the image at LOQ3 in the first data 706. The data for representing the image at LOQ3 in the first data 706 is the same as the data for representing the image at LOQ3 in the first data 602 described above with reference to FIG. 6.

As such, the encoder device 108 fully encodes the original image so that the decoder device 110 can recover the original image.

The decoder device 110 therefore receives data useable to generate data for representing the image at a first level of quality, for example at LOQ1 or LOQ2. The decoder device 110 also receives enhancement data useable to generate data for representing the image at a second level of quality, for example LOQ2 or LOQ3, based on the data for representing the image at the first level of quality, LOQ1 or LOQ2.

Figure 8:
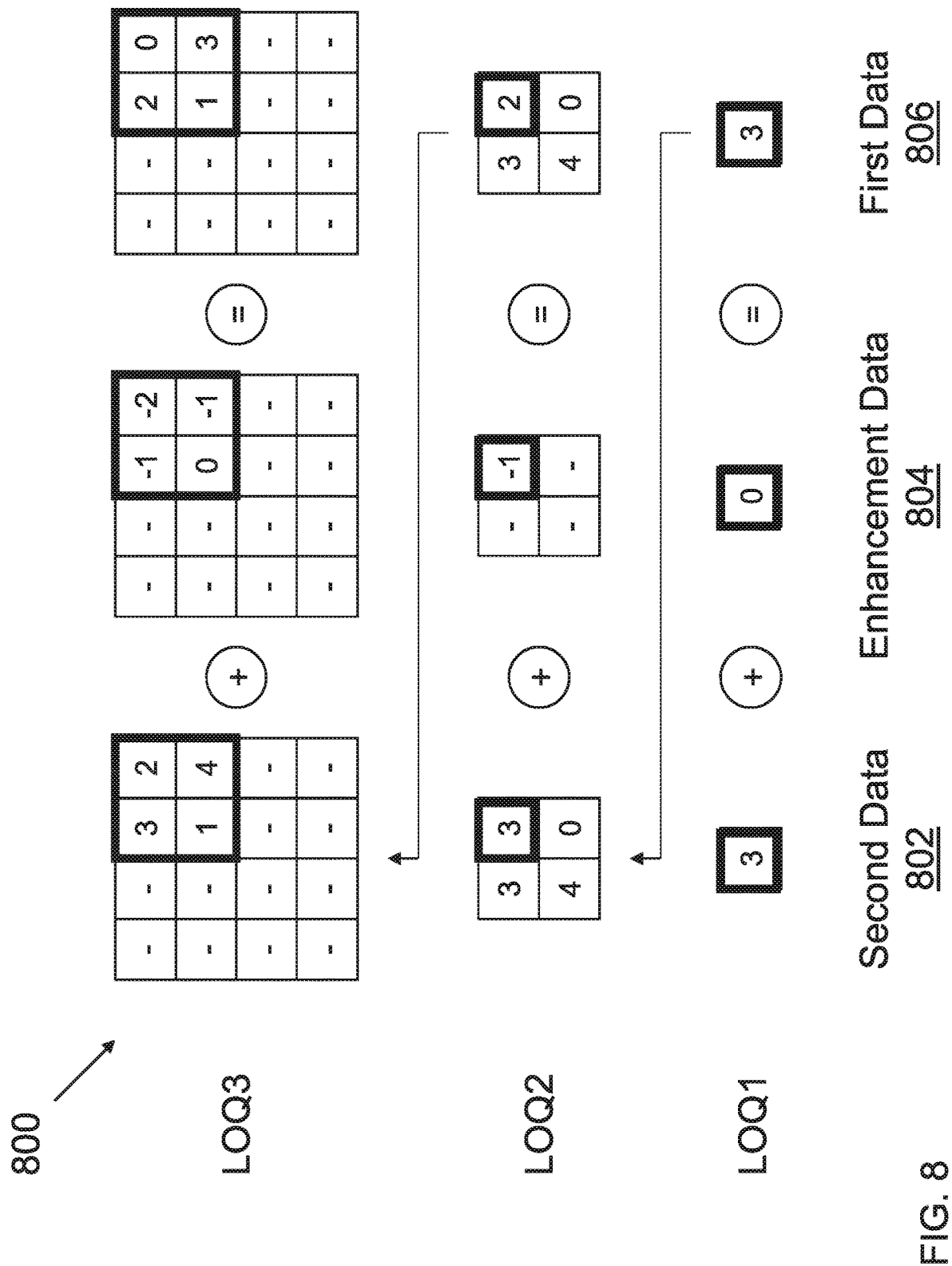
FIG. 8 shows schematically another example of data useable in a data signal processing system.

Referring to FIG. 8, there is shown example data 800 associated with the data signal processing system 100. In this example, the data 800 is obtained by the decoder device 110. In this example, the data 800 is related to data for representing an image at different levels of quality.

The example data 800 includes second data 802, enhancement data 804 and first data 806.

In this example, the decoder device 110 receives the same data as described above with reference to FIG. 7 from the encoder device 108. However, the decoder device 110 only uses a portion of the enhancement data 804 corresponding to a target region of the image. In this example, regions of interest in the data for representing the image corresponding to the target region, and the associated portions of the enhancement data 804, are shown using a thickened boundary line.

In this example, the decoder device 110 uses the data for representing the image at LOQ1 in the second data 802 and the enhancement data 804 at LOQ1 to generate the data for representing the image at LOQ1 in the first data 806. The decoder device 110 then upsamples the data for representing the image at LOQ1 in the first data 806 to generate the data for representing the image at LOQ2 in the second data 802. As only one portion of the enhancement data 804 at LOQ2 is associated with the region of interest in the data for representing the image at LOQ2 in the second data 802, that portion of the enhancement data 804 at LOQ2 is selected and is used along with the data for representing the image at LOQ2 in the second data 802 to generate the data for representing the image at LOQ2 in the first data 806. As the decoder device 110 used only the selected portion of the enhancement data 804 at LOQ2 to generate the data for representing the image at LOQ2 in the first data 806, only one element in the data for representing the image at LOQ2 in the second data 802 has been enhanced using the selected portion of the enhancement data 804 at LOQ2. In particular, the value of the bottom right element of the data for representing the image at LOQ2 in the first data 806 has a value of "0" whereas the enhanced (or 'corrected') value of that element is "1". In this example, the decoder device 110 only upsamples the region of interest in the data for representing the image at LOQ2 in the first data 806 to generate the data for representing the image at LOQ3 in the second data 802 at LOQ3. In this example, the decoder device 110 does not upsample any regions of the data for representing the image at LOQ2 in the first data 806 other than the region of interest. In other examples, the decoder device 110 may upsample one or more regions of the data for representing the image at LOQ2 in the first data 806 other than the region of interest.

As only one portion of the enhancement data 804 at LOQ3 is associated with the region of interest in the data for representing the image at LOQ3 in the second data 802, that portion of the enhancement data 804 at LOQ3 is selected and is used along with the values in the region of interest in the data for representing the image at LOQ3 in the second data 802 to generate the values in the region of interest in the data for representing the image at LOQ3 in the first data 806. The values in the region of interest in the data for representing the image at LOQ3 in the first data 806 are the same as the values in the corresponding region in the data for representing the image at LOQ 3 in the first data 602 described above with reference to FIG. 6.

In this example, the region of interest in the data for representing the image at LOQ3 in the first data 806 is the data for representing the target region of the image at a target level of quality. In this example, the region of the data for representing the image at LOQ2 in the first data 806 other than the region of interest is data for representing a further region of the image at a level of quality lower than the target level of quality.

The decoder device 110 therefore receives data useable to generate data for representing a data signal at a first level of quality, for example at LOQ1. The decoder device 110 also receives enhancement data useable to generate data for representing the data signal at a second level of quality, for example at LOQ3, based on the representation of the data signal at the first level of quality, LOQ1. The decoder device 110 generates data for representing a target region of the data signal at a target level of quality, for example LOQ2 or LOQ3, using a selected portion of the received enhancement data. The selection portion of the received enhancement data is associated with the target region of the data signal. The decoder device 110 generates data for representing a further region of the data signal at a level of quality lower than the target level of quality, for example at LOQ1 or LOQ2.

Since, in this example, the resolution of the data for representing the image at LOQ3 is different from the resolution of the data for representing the image at LOQ2, some or all of the data output by the decoder device 110 may need to be upsampled and/or modified in another way for display to the viewer.

For ease of explanation, assuming the display resolution were 4×4, the generated values in the region of interest in the data for representing the image at LOQ3 in the first data 806, comprising four values, may be used for display. Additionally, the region of the data for representing the image at LOQ2 in the first data 806 other than the region of interest, comprising three values, may be upsampled to generate twelve values, thus resulting in sixteen values in total for display. In reality, the display resolution is likely to be much higher than 4×4 and may not have equal dimensions.

Assuming the display resolution were 8×8, the region of interest in the data for representing the image at LOQ3 in the first data 806, comprising four values, may be upsampled once, generating sixteen values. The region of the data for representing the image at LOQ2 in the first data 806 other than the region of interest, comprising four values, may be upsampled twice to generate 48 values, thus resulting in 64 values in total for display. Again, in reality the display resolution is likely to be much higher than 8×8 and may not have equal dimensions.

As indicated above, in reality, display resolutions may be much higher than the 4×4 and 8×8 resolutions provided in the examples described above. For example, the display resolution may be 1920×540. Furthermore, although examples have been provided above in which the display resolution has equal dimensions (for example 4×4 and 8×8), display resolutions may have unequal dimensions and hence may be non-square, for example for widescreen displays.

Figure 9:
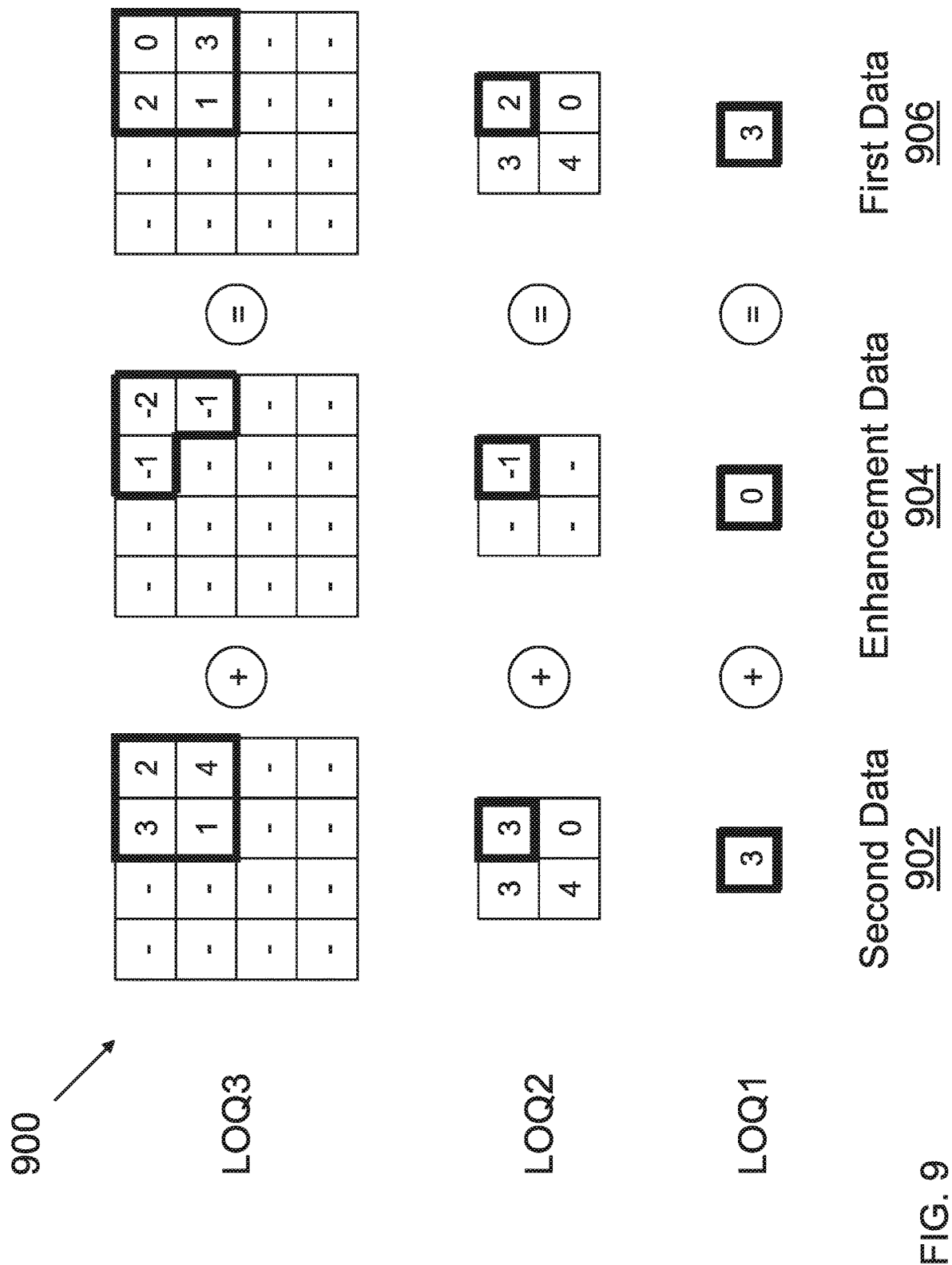
FIG. 9 shows schematically another example of data useable in a data signal processing system.

Referring to FIG. 9, there is shown example data 900 associated with the data signal processing system 100. In this example, the data 900 is obtained by the decoder device 110. In this example, the data 900 is related to data for representing an image at different levels of quality.

The example data 900 includes second data 902, enhancement data 904 and first data 906.

In this example, the decoder device 110 receives the same data as described above with reference to FIGS. 7 and 8 from the encoder device 108. However, the decoder device 110 only uses a portion of the enhancement data 904 associated with a target region of the image.

In this specific example, the decoder device 110 does not use all of the enhancement data 904 at LOQ3 that could be used to enhance the region of interest in the data for representing the image at LOQ3 in the second data 902. In this example, the portion of the enhancement data at LOQ3 selected by the decoder device 110 is associated with a sub-level of LOQ3, for example sub-level $LOQ3_3$. In particular, the decoder device 110 has not selected enhancement data that could be used to enhance the value of "1" at the bottom left of the data for representing the image at LOQ3 in the second data 902. This is the case even though such enhancement data is available to the decoder device 110 and is within a portion of the enhancement data associated with the region of interest in the data for representing the image at LOQ3 in the second data 902. The decoder device 110 may select which enhancement data associated with the region of interest is to be used based on the value(s) of such enhancement data. For example, enhancement data that has a value of or close to zero may not be selected for use, as the contribution of such enhancement data in changing the data for representing the image at LOQ3 in the second data 902 may be less significant than enhancement data having values further from zero.

Although, in this example, the accuracy of the values in the region of interest in the data for representing the image at LOQ3 in the first data 906 is lower than that in the region of interest in the data for representing the image at LOQ3 in the first data 806 shown in FIG. 8, the decoder device 110 has traded off such accuracy based on one or more other considerations. For example, the decoder device 110 may have traded off accuracy as a result of entering into a power-saving mode.

As such, a layer in the hierarchical data signal processing arrangement 200, 300 may be subdivided into multiple sub-layers, with each sub-layer containing data allowing an incremental number of data signal elements to be enhanced or corrected using the enhancement data associated with that sub-layer.

The decoder device 110 may be configured to use some or all of the enhancement data associated with the sub-layers to generating the data for representing the target region at the target level of quality based on one or more operating modes of the decoder device. The decoder device 110 and/or the second apparatus 104 may have several different operating modes. In some modes, for example a power-saving mode, only selected layers and/or sub-layers are decoded and used.

The decoder device 110 may be configured not to use a portion of enhancement data associated with at least one sub-layer in a first operating mode of the decoder device 110. The first operating mode may be a power-saving mode. For example, all sub-layers of lower levels of quality and no sub-layers on higher levels of quality may be used. Other combinations of uses of sub-layers from different levels could be used.

The decoder device 110 may be configured to use a portion of enhancement data associated with all sub-layers in a second operating mode of the decoder device 110. The decoder device 110 may be configured to use a portion of enhancement data associated with at least one sub-layer of the first and second layers in a third operating mode of the decoder device 110. For example, a single sub-layer may be used for each level of quality.

In a specific example, if the first layer, which is associated with a lower definition, has three sub-layers and the second layer, which is associated with a higher definition, also has three sub-layers, the decoder device 110 may choose to decode only the lowest sub-layer in the first and second layers in a power saving mode and to decode all three sub-layers of the first and second layers in a full power mode. Image processing conducted in this way gives a lower quality of image than if the fully encoded image were fully decoded, but may represent a defined and acceptable trade-off, for example for power-saving gains.

Figure 10:
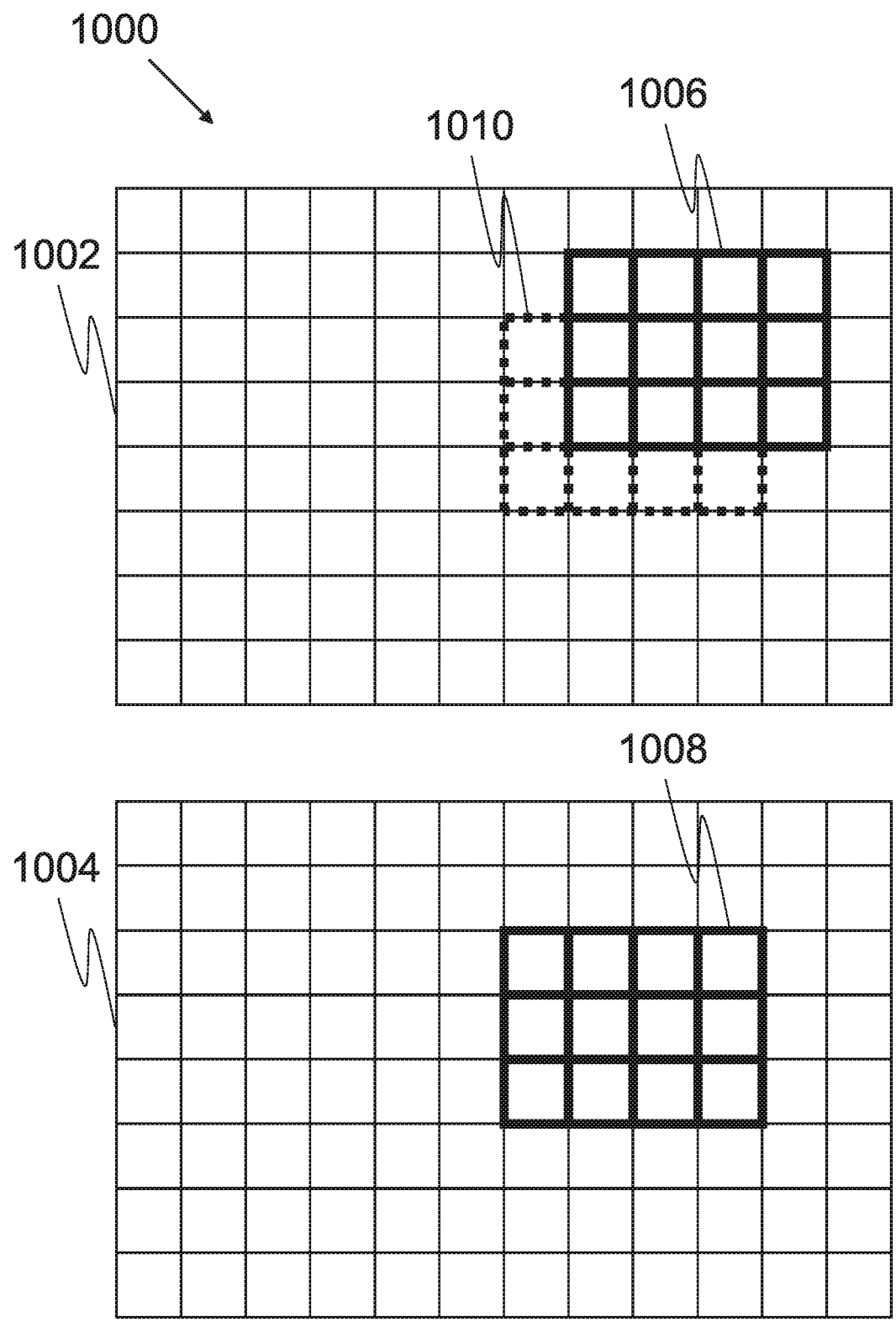
FIG. 10 shows schematically an example of a plurality of images.

Referring to FIG. 10, there is shown an example of a plurality of images 1000. The plurality of images 1000 includes a first image 1002 associated with a first time $t_1$ and a second image 1004 associated with a second time $t_2$. The first and second images 1002, 1004 may for example be comprised in a video sequence.

The first image 1002 has a first target region 1006 and the second image 1004 has a second target region 1008. The position of the first target region 1006 in the first image 1002 is different from the position of the second target region 1008 in the second image 1004. The position of the target region is therefore dynamic and not static in this example.

In some examples, the position of the target region changes based on where in the image, or sequence of images, the viewer is looking. For example, the position of the target region may change based on the field of view of the viewer and/or one or more gaze locations of the viewer in the image. The field of view of the viewer is the extent of an image or environment that is visible to the viewer at a given moment. The field of view may be a property of an external apparatus, for example a head-mounted display (HND), or of the human eyes. In the example of the human eyes, the field of view may be defined as the number of degrees of visual angle during stable fixation of the eyes. Movement of the eyes does not change the field of view. In contrast, a gaze or fixation location can depend on the movement of the viewer's eyes around an image. The gaze location is the location in the image where the viewer is directing the centre of their gaze at a given moment. The gaze location is therefore located within the field of view of the viewer. The gaze location may be based on the centre of the retina of the eye of the viewer. In addition to the gaze location, the field of view also comprises a peripheral field that surrounds the gaze location at a given moment.

The decoder device 110 may be configured to receive data associated with a field of view associated with a viewer and use the data associated with the field of view to identify the target region. The decoder device 110 may be configured to select the target region so as to be in the field of view. As such, the decoder device 110 can align the target region with where the viewer is looking or is likely to be looking to allow a high quality region of the image to be displayed to the viewer where they are looking. The decoder device 110 may be configured to select at least part of the further region so as to be in the field of view. Where the at least part of the further region is in the field of view of the user, the decoder device 110 may generate data for representing the at least part of the further region at a level of quality intermediate the highest and lowest level of qualities as it is visible to the viewer and having the lowest level of quality may detract from user experience. The decoder device 110 may be configured to receive data associated with one or more gaze positions associated with a user and use the data associated with the one or more gaze positions to identify the target region. The decoder device 110 may therefore align the target region with where the user is looking and/or is likely to be looking.

For applications, the target region 1006, 1008 behaves like a sliding (or 'moving') window wherein the decoder device 110 decodes a higher quality image or video in a sliding window manner. The sliding window may contain the one or more gaze points of the viewer.

In this example, the images 1002, 1004 comprise a plurality of tiles. Enhancement data is associated with the tiles. The enhancement data may be used to generate data for representing one or more regions of the images 1002, 1004 at a relatively high level of quality. For example, the enhancement data may be used to generate data for representing the target regions 1006, 1008 at relatively high levels of quality compared to the level of quality associated with the further regions associated with the tiles outside the target regions 1006, 1008. The target regions 1006, 1008 may correspond to visible (or 'viewable') sections of the images 1006, 1008. In the context of virtual reality for example, as the viewer moves, the target region moves in a moving (or 'sliding') window manner. In some examples, when the amount of movement or deviation in viewing by the viewer exceeds a threshold amount, one or more tiles are added to and/or removed from the target region. Thus, when the viewer moves, the moving window moves tile by tile. Region 1010 in the first image 1002 corresponds to a group of tiles that are not in the target region 1006 of the first image 1002 but are in the target region 1008 of the second image 1004. The decoder device 110 may be able to predict which regions and corresponding tiles will be added to the target region in a subsequent image and generate data for representing the regions at a desired level of quality once such a prediction has been made. Using this prediction approach may decrease the amount of time to generate the data for representing the target region in the subsequent image. The decoder device 110 may not need to generate data for representing any region of overlap of the target region between subsequent images as data for representing the region of overlap may already be available to the decoder device 110 in respect of a previous image. Such overlapping data could for example be cached for a given number of subsequent images and fetched from the cache if needed.

As such, even though high quality image or video data is available to the decoder device 110 for the whole image or video, the decoder device 110 only decodes the viewable section to a relatively high level of quality, for example to the maximum level of quality, thereby saving power and other resources at the decoder device 110 and/or the second apparatus 104. With scalable video coding techniques similar to those described above, a high quality layer may be defined per tile and the decoder device 110 device fetches data relating to a base layer and to the high quality layer for tiles in focus, thereby saving bandwidth, power and processing capability compared to fetching and processing such data for all tiles in the image. The decoder device 110 may determine a position of a target region in a subsequent image dependent on the field of view and/or one or more gaze positions of the viewer at a point in time associated with the subsequent image.

Further, in the context of virtual reality applications of the technology described above, a viewer may be physically very close to the display screen. It may therefore be desirable to have high resolution images or video, particularly where the display screen has a high display resolution, so that the viewer does not notice defects in the image or video that may be apparent at lower levels of quality or resolution. This may place restrictions on the hardware or software that can be used in such applications because of the hardware and/or software and/or other requirements to be able to handle data at such a high level. For example, it may be desired to send a UHD or 4K video stream to the decoder device 110 and/or second apparatus 104. The decoder device 110 and/or second apparatus 104 would need to be able to download or stream that video and would need the capability to decode and display the video stream at 4K. There may be a limited demand for or availability of such devices. In examples described above, the decoder device 110 may not need a 4K decoder to be able to handle such video data. Instead, decoder device 110 can decode video data at a lower level of quality, for example HD, and use upscaling and enhancement data to generate a representation of the video at the 4K level of quality. Through the use of scalable encoding, this may also result in more efficient bandwidth usage, since it is not required to send a 4K video stream across a network, even for a specific image tile or tiles. In some examples, the decoder device 110 decodes a relatively low quality 4K video stream and uses enhancement data to generate a relatively high quality 4K representation of the video stream. The relatively low quality 4K stream and the relatively high quality 4K representation may be associated with different sub-layers of a hierarchical data processing arrangement, as described above.

Example Apparatus

Figure 11:
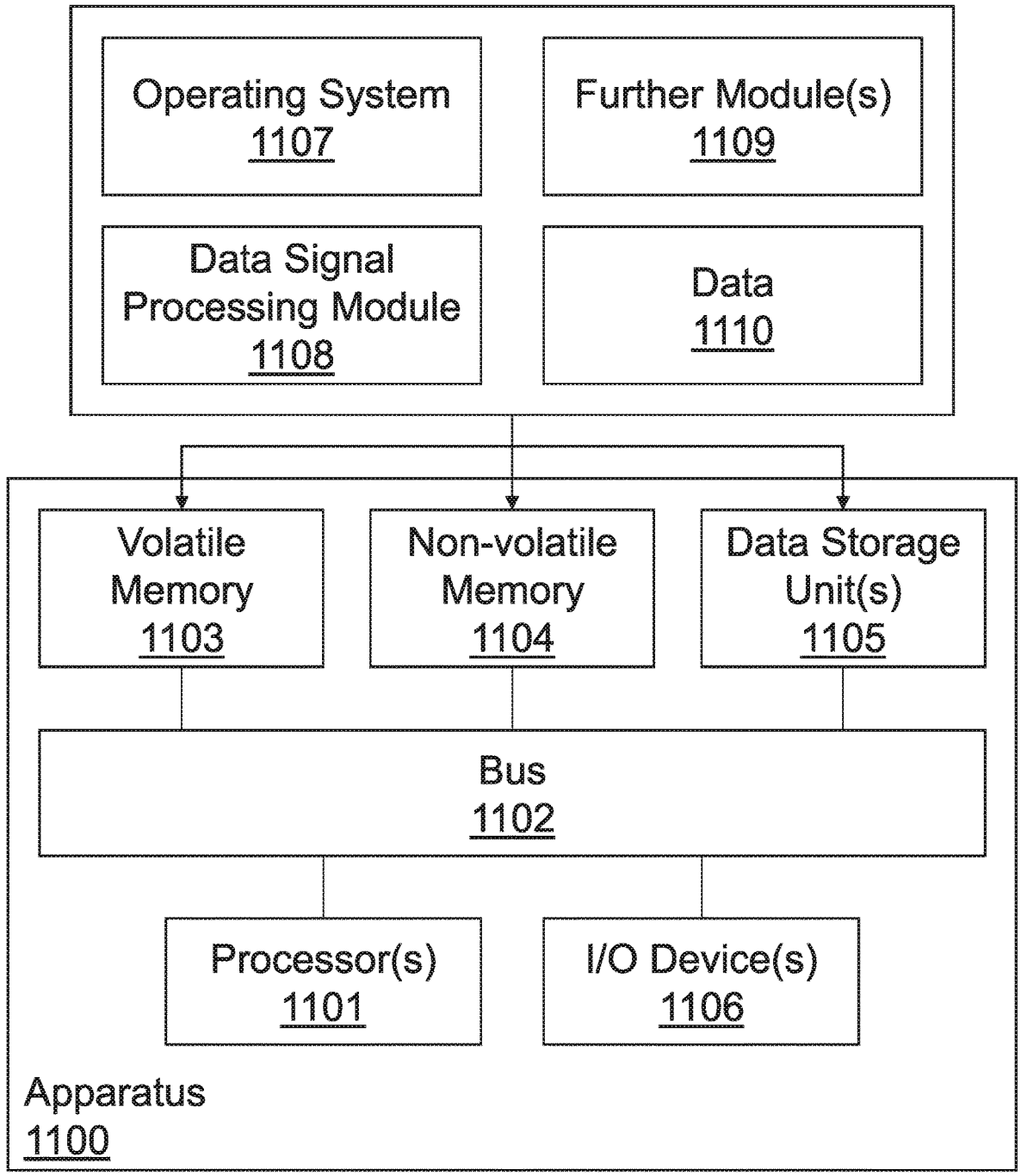
FIG. 11 shows a schematic block diagram of an example of an apparatus.

Referring to FIG. 11, there is shown a schematic block diagram of an example of an apparatus 1100.

In an example, the apparatus 1100 comprises a decoder device.

Examples of apparatus 1100 include, but are not limited to, a mobile computer, a personal computer system, a wireless device, base station, phone device, desktop computer, laptop, notebook, netbook computer, mainframe computer system, handheld computer, workstation, network computer, application server, storage device, a consumer electronics device such as a camera, camcorder, mobile device, video game console, handheld video game device, a peripheral device such as a switch, modem, router, etc., or in general any type of computing or electronic device.

In this example, the apparatus 1100 comprises one or more processors 1101 configured to process information and/or instructions. The one or more processors 1101 may comprise a central processing unit (CPU). The one or more processors 1101 are coupled with a bus 1102. Operations performed by the one or more processors 1101 may be carried out by hardware and/or software. The one or more processors 1101 may comprise multiple co-located processors or multiple disparately located processors.

In this example, the apparatus 1100 comprises computer-useable volatile memory 1103 configured to store information and/or instructions for the one or more processors 1101. The computer-useable volatile memory 1103 is coupled with the bus 1102. The computer-useable volatile memory 1103 may comprise random access memory (RAM).

In this example, the apparatus 1100 comprises computer-useable non-volatile memory 1104 configured to store information and/or instructions for the one or more processors 1101. The computer-useable non-volatile memory 1104 is coupled with the bus 1102. The computer-useable non-volatile memory 1104 may comprise read-only memory (ROM).

In this example, the apparatus 1100 comprises one or more data-storage units 1105 configured to store information and/or instructions. The one or more data-storage units 1105 are coupled with the bus 1102. The one or more data-storage units 1105 may for example comprise a magnetic or optical disk and disk drive or a solid-state drive (SSD).

In this example, the apparatus 1100 comprises one or more input/output (I/O) devices 1106 configured to communicate information to and/or from the one or more processors 1101. The one or more I/O devices 1106 are coupled with the bus 1102. The one or more I/O devices 1106 may comprise at least one network interface. The at least one network interface may enable the apparatus 1100 to communicate via one or more data communications networks. Examples of data communications networks include, but are not limited to, the Internet and a Local Area Network (LAN). The one or more I/O devices 1106 may enable a user to provide input to the apparatus 1100 via one or more input devices (not shown). The one or more input devices may include for example a remote control, one or more physical buttons etc. The one or more I/O devices 1106 may enable information to be provided to a user via one or more output devices (not shown). The one or more output devices may for example include a display screen.

Various other entities are depicted for the apparatus 1100. For example, when present, an operating system 1107, data signal processing module 1108, one or more further modules 1109, and data 1110 are shown as residing in one, or a combination, of the computer-usable volatile memory 1103, computer-usable non-volatile memory 1104 and the one or more data-storage units 1105. The data signal processing module 1108 may be implemented by way of computer program code stored in memory locations within the computer-usable non-volatile memory 1104, computer-readable storage media within the one or more data-storage units 1105 and/or other tangible computer-readable storage media. Examples of tangible computer-readable storage media include, but are not limited to, an optical medium (e.g., CD-ROM, DVD-ROM or Blu-ray), flash memory card, floppy or hard disk or any other medium capable of storing computer-readable instructions such as firmware or microcode in at least one ROM or RAM or Programmable ROM (PROM) chips or as an Application Specific Integrated Circuit (ASIC).

The apparatus 1100 may therefore comprise a data signal processing module 1108 which can be executed by the one or more processors 1101. The data signal processing module 1108 can be configured to include instructions to implement at least some of the operations described herein. During operation, the one or more processors 1101 launch, run, execute, interpret or otherwise perform the instructions in the signal processing module 1108.

Although at least some aspects of the examples described herein with reference to the drawings comprise computer processes performed in processing systems or processors, examples described herein also extend to computer programs, for example computer programs on or in a carrier, adapted for putting the examples into practice. The carrier may be any entity or device capable of carrying the program.

It will be appreciated that the apparatus 1100 may comprise more, fewer and/or different components from those depicted in FIG. 11.

The apparatus 1100 may be located in a single location or may be distributed in multiple locations. Such locations may be local or remote.

The techniques described herein may be implemented in software or hardware, or may be implemented using a combination of software and hardware. They may include configuring an apparatus to carry out and/or support any or all of techniques described herein.

Example Application

Figure 14:
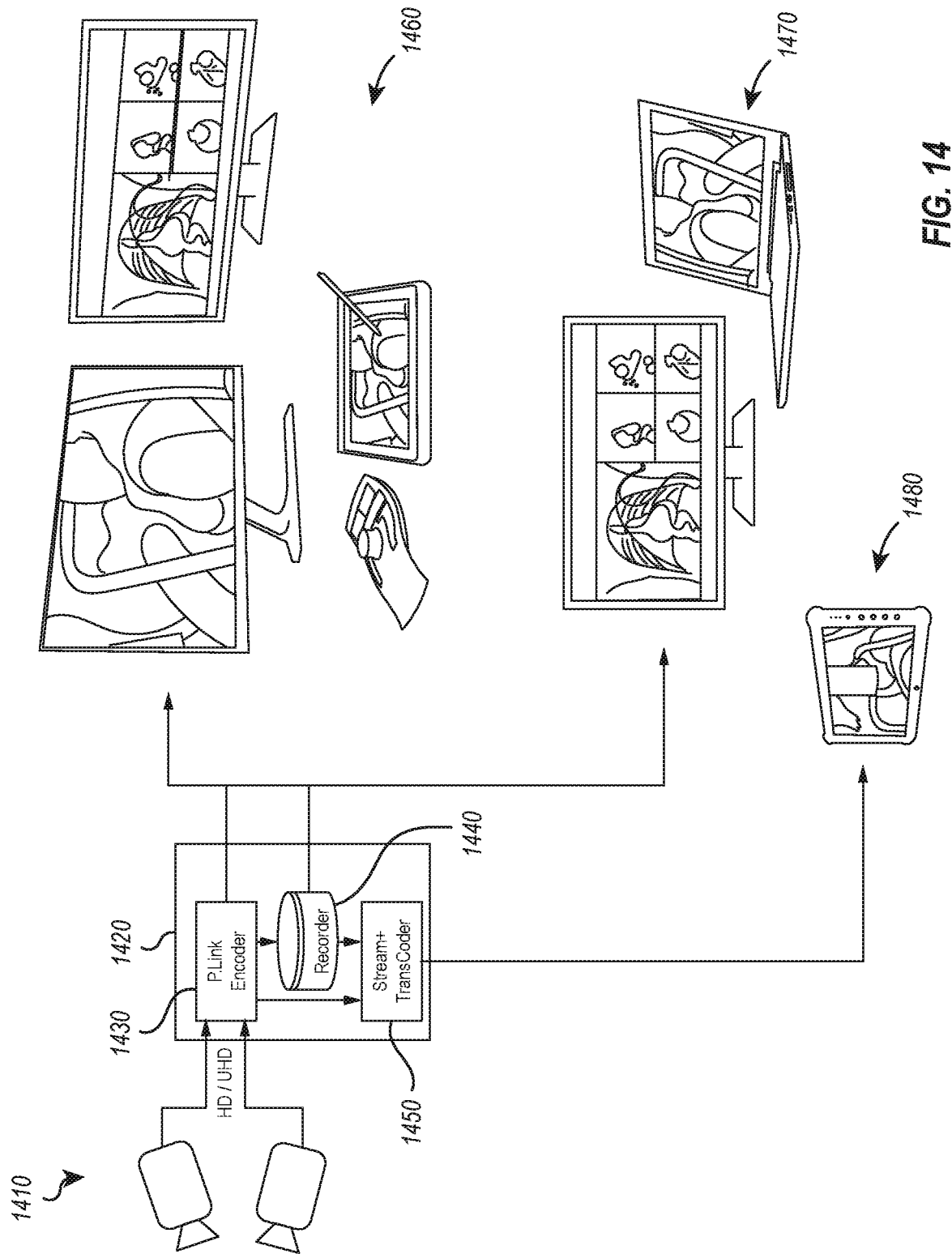
FIG. 14 shows an example system for remote guidance on a medical procedure.

FIG. 14 shows an example application of the principles described herein within telemedicine. The context may be a surgical operation that requires remote guidance, e.g. from one or more specialists that are geographically remote from the surgery site, or that cannot be present for technical or medical reasons. In this example there are a plurality of video recording devices 1410 to capture a video recording of the surgical operation. The video recording devices 1410 may comprise operating theatre video cameras. The plurality of video recording devices 1410 may provide video at a common resolution or at differing resolutions. The resolutions may be one or more of SD, HD and UHD. The video recording devices are communicatively coupled to a hierarchical encoder 1430 (labelled "P. Link Encoder" in the Figure), which may operate as described with reference to the encoders herein. The hierarchical encoder 1430 may encode video streams from the video recording devices using a hierarchical encoding scheme such as SMPTE VC-6.

An output of the hierarchical encoder is receivable by local computing 1460, 1470 and/or display devices 1460, 1470, which include desktop computing devices, monitors with built-in decoders, tablets and other devices. The receiving devices (1460 and 1470) may comprise implementations of the decoder devices described herein. An encoded stream from the hierarchical encoder may be best received over higher speed local or wide area network connections.

FIG. 14 also shows an output of the hierarchical encoder 1430 being received by a recorder 1440, which stores the output of the hierarchical encoder 1430 as one or more files. For example, the recorder 1440 may form part of an HSM system as described above. Data stored by the recorder 1440 may be viewable at a later point in time, e.g. for audit or training purposes.

An output of the hierarchical encoder 1430 is also received by a transcoder 1450. The transcoder 1450 may convert from an SMPTE VC-6 encoding to a MPEG-5, Part 2 encoding that is better suited to variable quality wide area networks such as the Internet. An output of the transcoder 1450 may thus comprise an MPEG-5, Part 2 (LCEVC) encoded stream that may be received and decoded by a mobile computing device 1480. MPEG-5, Part 2 (LCEVC) may allow older legacy devices to receive and decode the base codec (e.g. at SD resolution) but also allow newer devices increased functionality via the use of an enhancement codec (e.g. higher resolution, zooming, panning etc.).

The configuration of FIG. 14 allows a single architecture to be used for all users, e.g. mobile devices, desktop workstations and server devices may all receive an output of the architecture and may similarly decode hierarchical data, e.g. to allow navigation in a sequence, panning, zooming, quick navigation backwards and forwards (e.g. by just viewing a lower resolution layer that be quickly rendered). The hierarchical encoding allows low latency, as network issues result in a degraded resolution rather than buffering and an interrupted stream as with comparative video encoding. This may be vital for time sensitive procedures such as surgery (e.g. even if there are technical or network problems, a set of lower resolution layers may still be receivable and viewable, so advice may still be provided based on an uninterrupted data sequence). As described herein devices may receive the highest quality possible automatically, meaning all users easily get the best view of the data that they can. The solution may be able to easily scale with different network capabilities, e.g. encoded streams may be provided at between 1 Mbps to 250 Mbps per video camera.

FIG. 14 also shows how multiple video and/or image streams may be hierarchically encoded and then decoded for viewing at different levels of quality. FIG. 14 shows a display device (1460, 1470, 1480) that is viewing decoded video from the operating theatre, as well as images of the region being operated on (e.g. CT scans or X-Rays) and computer models. Multiple streams may be more easily managed as they may all be received at lower resolution levels and then received and decoded at higher resolutions on demand, e.g. when viewed and/or when a region of interest is viewed.

Figure 15:
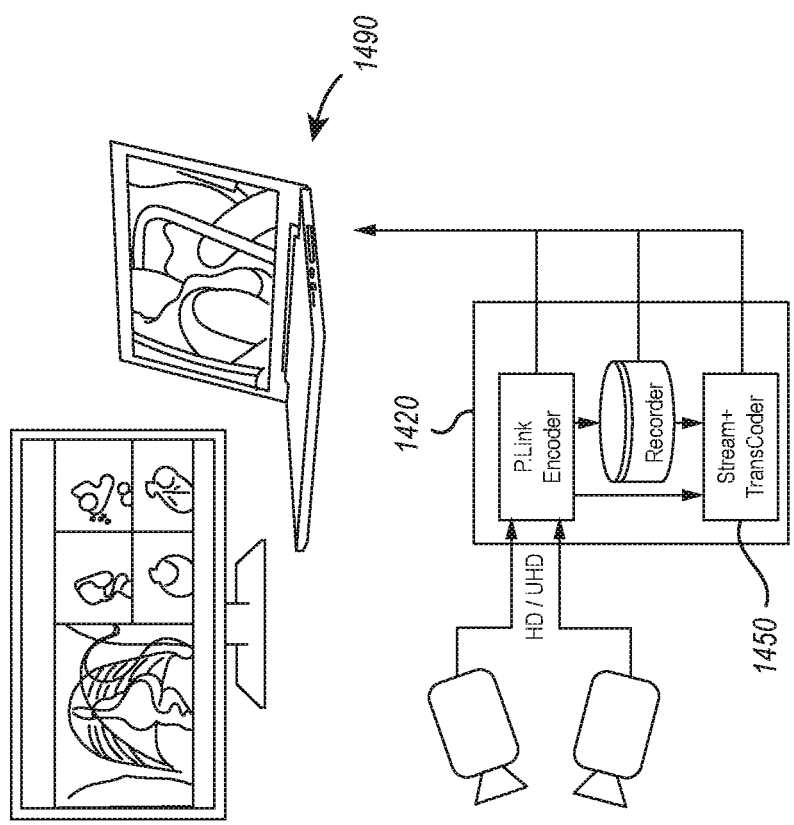
FIG. 15 shows a number of ways a computing device may view a stream of data.

For good local area and wide area connections, a highest possible quality may be viewable and variations on live playback may be enabled (e.g. replay of live events). Frame by frame indexing may be easy using lower level representations, as may panning and zooming within a particular data or video feed. Multiple views and multiple resolutions may be easily integrated, as may 3D interaction devices, touch-screens and drawing tablets (1460, 1470, 1480). Both live and recorded events may have these advantages, where the latter may be provided by accessing a stored hierarchical encoding on the recorder 1440. Quality of a data or video feed may scale with an available connection and adaptations may be made for constrained connections, e.g. a desktop or laptop device 1490 may have the option of receiving data from the hierarchical encoder, the recorder and/or the transcoder based on circumstances, this is illustrated in FIG. 15. This provides increased flexibility in terms of location, device and connection. Mobile devices may use the transcoded output to receive an app-based low latency feed that is provided at the highest quality despite constrained communication links.

The configurations of FIGS. 14 and 15 may also be used for teaching, where replaying the encoded video from the recorder may use a same system and interface as watching one or more live streams. Recorded data may thus have the same abilities (e.g. for panning/zooming/region of interest rendering etc.) as live data.

Using a hierarchical coding scheme may also provide advantages for later analysis of the video. For example, AI analysis such as object recognition may be advantageously applied, as for example described in PCT/GB2020/050312, which is incorporated herein by reference. In these cases, different layers at different resolutions may be transmitted, communicated and decoded as required, with analysis being performed on different layers in parallel, and on residual data as well as reconstructed video. In certain cases, AI analysis may be limited to a region of interest, and so may use the efficient region of interest decoding approaches discussed herein. Human annotation of data may also be facilitated in a similar manner, and HSM may provide faster access and reduced cost storage.

Example Advantages

Use of a hierarchical coding scheme as described herein allows the time value of remote guidance information to be maintained by presenting the information when it is required and gracefully scaling up and down resolutions when network or resource constraints present themselves.

Storage of an encoded full resolution in an HSM system, i.e. using the hierarchical coding schemes described herein, may be performed efficiently, especially when residual data is used to encode certain layers. A tier-based approach may facilitate storage and retrieval, e.g. files may be accessed and downloaded in tiers, and file transfer can be adapted to datalink demand by transferring increasing resolutions during times of spare capacity.

In certain examples, a common stream or file may be generated but different devices may receive and/or decode portions of the stream based on their requirements, e.g. a full UHD source may be encoded, but only those portions required to render an HD view may be received and decoded for viewing on an HD monitor. Additionally, or alternatively, low-resolution versions of multiple sources may be received and rendered on a single monitor, and the higher resolution portions of the hierarchical stream may only need to be downloaded and/or decoded if they are being viewed at a high resolution. Navigation within a sequence, panning, zooming and indexing forwards and backwards may only require a region of the image/video to be transferred. Resolutions may dropped during network contention while allowing the user to select the area of interest that is really important to enable continued operations. Teaching operations can also use all the benefits of live and near live encodings.

A method of providing telepresence using a tier-based hierarchical data coding scheme is described. Encoding and decoding methods and devices may be provided.

The method may comprise providing an enlarged portion of a data stream for use in telepresence. The method may comprise: upon reception of an input from a user, sending a signal to a server to fetch a target portion of the image; receiving, from the server, an encoded version of the target portion, the encoded version being encoded using a tier-based hierarchical data coding scheme; decoding said encoded version of the target portion to reconstruct a decoded version of the target portion; displaying said decoded version of the target portion.

A system for remote guidance may comprise a hierarchical encoder that receives one or more data feeds, encodes said data feeds using a tier-based hierarchical data coding scheme, and instructs distribution of the resulting encoding data feeds to a plurality of viewing devices, wherein the viewing devices are able to decode the encoded data feeds at different levels of quality. The system for remote guidance may also comprise a recorder to store an output of the hierarchical encoder as a set of tier-based files representing different levels of quality. The encoded data feeds may comprise multiple encoded layers that enable one or more of panning, zooming, and region of interest selection, e.g. where different resolutions may be viewable by only receiving and/or decoding a portion of one or more layers.

Various measures (for example decoder devices, methods and computer programs) are provided. At a decoder, data useable to generate data for representing a data signal at a first level of quality is received. Enhancement data useable to generate data for representing the data signal at a second level of quality based on the data for representing the data signal at the first level of quality is received. The second level of quality is higher than the first level of quality.

Data for representing a target region of the data signal may be provided at a target level of quality is generated using a selected portion of the received enhancement data. The selected portion of the received enhancement data is associated with the target region of the data signal. The target level of quality is higher than the first level of quality. Data for representing a further region of the data signal at a level of quality lower than the target level of quality is generated.

The target level of quality may be the second level of quality.

The target level of quality may be between the first level of quality and the second level of quality.

The level of quality of the further region may be between the first level of quality and the target level of quality.

The decoder device may be configured to generate the data for representing the further region of the data signal using a selected further portion of the enhancement data. The selected further portion of the enhancement data may be associated with the further region of the data signal.

The level of quality of the further region may be the first level of quality.

The further region may at least partly surround the target region.

Data associated with a field of view and/or data associated with one or more gaze positions may be used to identify the target region of the data signal.

The target region of the data signal may be selected so as to be in the field of view.

At least part of the further region of the data signal may be selected so as to be in the field of view.

The field of view and/or the one or more gaze positions may be monitored at multiple points in time. A position of a target region in a subsequent data signal may be determined dependent on the field of view and/or the one or more gaze positions at a point in time associated with the subsequent data signal.

The target region of the data signal may be associated with one or more data signal tiles and the further region of the data signal may be associated with one or more data signal tiles. At least one of the data signal tiles associated with the further region may be within the target region in the subsequent data signal.

Data for representing the target region of the data signal at the first level of quality may be generated. The generated data for representing the target region of the data signal at the first level of quality may be used to generate the data for representing the target region of the data signal at the target level of quality.

Operation may be in accordance with a hierarchical data signal processing arrangement.

The hierarchical data signal processing arrangement may comprise at least one layer having a set of sub-layers. Each sub-layer may be associated with a respective level of quality.

Enhancement data associated with at least one of the sub-layers may not be used in a first operating mode of the decoder device.

Enhancement data associated with all of the sub-layers may be used to generate the data for representing the target region of the data signal at a target level of quality in a second operating mode of the decoder device.

Operation may be in accordance with a hierarchical data signal processing arrangement.

The hierarchical data signal processing arrangement may comprise a first layer having a first set of sub-layers and a second layer having a set of sub-layers. Each sub-layer may be associated with a respective level of quality.

Enhancement data associated with at least one sub-layer of the first and second layers may be used to generate the data for representing the target region of the data signal at the target level of quality in a third operating mode of the decoder device.

The first level of quality may correspond to a level of quality associated with the lowest sub-layer in the hierarchical data signal processing arrangement.

The second level of quality may correspond to a level of quality associated with the highest sub-layer in the hierarchical data signal processing arrangement.

The target level of quality may correspond to a level of quality associated with a sub-layer between the highest sub-layer and the lowest sub-layer in the hierarchical data signal processing arrangement.

The data signal may comprise image data.

The data signal may comprises video data.

The target region of the data signal may be identified.

The portion of the enhancement data associated with the target region of the data signal may be selected.

A decoder device may be comprised in virtual reality equipment, medical imaging equipment, machine vision equipment and/or or a mobile communications device.

Virtual reality equipment may comprise the decoder device.

Medical imaging equipment may comprise the decoder device.

Machine vision equipment may comprise the decoder device.

A mobile communications device may comprise the decoder device.

The above embodiments are to be understood as illustrative examples. Further embodiments are envisaged.

In some examples described above, the decoder device 110 receives the fully encoded data from the encoder device 108 via the data communications network 106. In further examples, the decoder device 110 retrieves such data from local memory, for example non-volatile memory. In further examples, the decoder device 110 retrieves such data from a removable storage medium, for example a Compact Disc Read-Only Memory (CD-ROM), Digital Versatile Disc (DVD), Blu-Ray etc.

In some examples described above, the data signal processing system 100 processes image and/or video data. In further examples, the data signal processing system 110 processes other types of data signal, such as audio and/or volumetric data. In such systems, it may be desired to enhance a level of quality of a target region of the data processed by the system. In the case of audio data, a target region may comprise a particular frequency and/or temporal range of the audio data. In the case of volumetric data, such as "three-dimensional" medical imaging data, a target region may be a region in the volumetric data which corresponds to a particular physical region of interest, for example an organ, foetus or tumour.

It is to be understood that any feature described in relation to any one embodiment may be used alone, or in combination with other features described, and may also be used in combination with one or more features of any other of the embodiments, or any combination of any other of the embodiments.

The invention claimed is:

1. Virtual reality equipment comprising a decoder device configured to:
   receive data useable to generate first data for representing a data signal at a first level of quality;
   receive enhancement data useable to generate data for representing the data signal at a second level of quality based on the first data for representing the data signal at the first level of quality, the second level of quality being higher than the first level of quality;

generate data for representing a target region of the data signal at a target level of quality using a selected portion of the received enhancement data, the selected portion of the received enhancement data being associated with the target region of the data signal, the target level of quality being higher than the first level of quality; and generate data for representing a further region of the data signal at a level of quality lower than the target level of quality, wherein the enhancement data is configured to correct differences between one or more values of one or more elements in the first data for representing the data signal at the first level of quality and one or more corresponding values of one or more elements in second data for representing the data signal at the first level of quality, wherein the decoder device is configured to operate in accordance with a hierarchical data signal processing arrangement, the hierarchical data signal processing arrangement comprising a first layer having a first set of sub-layers and a second layer having a set of sub-layers, each sub-layer being associated with a respective level of quality, and wherein the decoder device is configured to use enhancement data associated with at least one sub-layer of the first and second layers to generate the data for representing the target region of the data signal at the target level of quality in a third operating mode of the decoder device.

2. The virtual reality equipment according to claim 1, wherein the target level of quality is the second level of quality, or wherein the target level of quality is between the first level of quality and the second level of quality.

3. The virtual reality equipment according to claim 1, wherein the level of quality of the further region of the data signal is between the first level of quality and the target level of quality.

4. The virtual reality equipment according to claim 1, wherein the decoder device is configured to generate the data for representing the further region of the data signal using a selected further portion of the enhancement data, the selected further portion of the enhancement data being associated with the further region of the data signal.

5. The virtual reality equipment according to claim 1, wherein the level of quality of the further region of the data signal is the first level of quality.

6. The virtual reality equipment according to claim 1, wherein the decoder device is configured to select the target region of the data signal so as to be in a field of view, and wherein the decoder device is configured to select at least part of the further region of the data signal so as to be in the field of view.

7. The virtual reality equipment according to claim 6, wherein the decoder device is configured to:

monitor the field of view and/or one or more gaze positions at multiple points in time; and determine a position of a target region in a subsequent data signal dependent on the field of view and/or the one or more gaze positions at a point in time associated with the subsequent data signal, optionally wherein the target region of the data signal is associated with one or more data signal tiles and the further region of the data signal is associated with one or more data signal tiles, wherein at least one of the data signal tiles associated with the further region of the data signal is within the target region in the subsequent data signal.

8. The virtual reality equipment according to claim 1, wherein the decoder device is configured to:

generate data for representing the target region of the data signal at the first level of quality; and use the generated data for representing the target region of the data signal at the first level of quality to generate the data for representing the target region of the data signal at the target level of quality.

9. The virtual reality equipment according to claim 1, wherein the decoder device is configured to operate in accordance with a hierarchical data signal processing arrangement, the hierarchical data signal processing arrangement comprising at least one layer having a set of sub-layers, each sub-layer being associated with a respective level of quality.

10. The virtual reality equipment according to claim 9, wherein the decoder device is configured not to use enhancement data associated with at least one of the sub-layers in a first operating mode of the decoder device, or wherein the decoder device is configured use enhancement data associated with all of the sub-layers to generate the data for representing the target region of the data signal at a target level of quality in a second operating mode of the decoder device.

11. The virtual reality equipment according to claim 9, wherein the first level of quality corresponds to a level of quality associated with the lowest sub-layer in the hierarchical data signal processing arrangement.

12. The virtual reality equipment according to claim 9, wherein the second level of quality corresponds to a level of quality associated with the highest sub-layer in the hierarchical data signal processing arrangement.

13. The virtual reality equipment according to claim 9, wherein the target level of quality corresponds to a level of quality associated with a sub-layer between the highest sub-layer and the lowest sub-layer in the hierarchical data signal processing arrangement.

14. The virtual reality equipment according to claim 1, wherein the decoder device is configured to identify the target region of the data signal.

15. The virtual reality equipment according to claim 1, wherein the decoder device is configured to select the portion of the enhancement data associated with the target region of the data signal.

16. The virtual reality equipment according to claim 1, wherein the differences between the one or more values of the one or more elements in the first data for representing the data signal at the first level of quality and the one or more corresponding values of the one or more elements in the second data for representing the data signal at the first level of quality result from downsampling and upsampling operations performed using the second data for representing the data signal at the first level of quality, the downsampling and upsampling operations having been performed to generate the first data for representing the data signal at the first level of quality.

17. A method comprising, at a decoder device:

receiving data useable to generate first data for representing a data signal at a first level of quality;

receiving enhancement data useable to generate data for representing the data signal at a second level of quality based on the first data for representing the data signal at the first level of quality, the second level of quality being higher than the first level of quality;

generating data for representing a target region of the data signal at a target level of quality using a selected portion of the received enhancement data, the selected portion of the received enhancement data being associated with the target region of the data signal, the target level of quality being higher than the first level of quality; and generating data for representing a further region of the data signal at a level of quality lower than the target level of quality, wherein the enhancement data is configured to correct differences between one or more values of one or more elements in the first data for representing the data signal at the first level of quality and one or more corresponding values of one or more elements in second data for representing the data signal at the first level of quality, wherein the decoder device is configured to operate in accordance with a hierarchical data signal processing arrangement, the hierarchical data signal processing arrangement comprising a first layer having a first set of sub-layers and a second layer having a set of sub-layers, each sub-layer being associated with a respective level of quality, and wherein the decoder device is configured to use enhancement data associated with at least one sub-layer of the first and second layers to generate the data for representing the target region of the data signal at the target level of quality in a third operating mode of the decoder device.

18. A non-transitory computer-readable medium having stored thereon computer executable instructions that when executed by a processor cause the processor to perform the following operations:

receive data useable to generate first data for representing a data signal at a first level of quality;

receive enhancement data useable to generate data for representing the data signal at a second level of quality based on the first data for representing the data signal at the first level of quality, the second level of quality being higher than the first level of quality;

generate data for representing a target region of the data signal at a target level of quality using a selected portion of the received enhancement data, the selected portion of the received enhancement data being associated with the target region of the data signal, the target level of quality being higher than the first level of quality; and generate data for representing a further region of the data signal at a level of quality lower than the target level of quality, wherein the enhancement data is configured to correct differences between one or more values of one or more elements in the first data for representing the data signal at the first level of quality and one or more corresponding values of one or more elements in second data for representing the data signal at the first level of quality, wherein the processor is configured to operate in accordance with a hierarchical data signal processing arrangement, the hierarchical data signal processing arrangement comprising a first layer having a first set of sub-layers and a second layer having a set of sub-layers, each sub-layer being associated with a respective level of quality, and wherein the processor is configured to use enhancement data associated with at least one sub-layer of the first and second layers to generate the data for representing the target region of the data signal at the target level of quality in a third operating mode of the decoder device.

* * * * *